United States Patent
Baumbach et al.

(10) Patent No.: US 12,144,976 B2
(45) Date of Patent: Nov. 19, 2024

(54) METHOD AND DEVICE FOR DETECTING A WEAR CONDITION OF A VENTRICULAR ASSIST DEVICE AND FOR OPERATING SAME, AND VENTRICULAR ASSIST DEVICE

(71) Applicant: KARDION GMBH, Stuttgart (DE)

(72) Inventors: Hardy Baumbach, Stuttgart (DE); Julian Kassel, Böblingen (DE); Inga Schellenberg, Stuttgart (DE); Ricardo Ehrenpfordt, Korntal-Münchingen (DE); Marc Schmid, Stuttgart (DE); Ahmad Mansour, Weil der Stadt (DE); Martina Budde, Karlsruhe (DE); Thomas Alexander Schlebusch, Renningen (DE)

(73) Assignee: Kardion GmbH, Stuttgart (DE)

( * ) Notice: Subject to any disclaimer, the term of this patent is extended or adjusted under 35 U.S.C. 154(b) by 1003 days.

(21) Appl. No.: 17/252,498

(22) PCT Filed: Jun. 21, 2019

(86) PCT No.: PCT/EP2019/066486
§ 371 (c)(1),
(2) Date: Jul. 27, 2021

(87) PCT Pub. No.: WO2019/243582
PCT Pub. Date: Dec. 26, 2019

(65) Prior Publication Data
US 2021/0346678 A1 Nov. 11, 2021

(30) Foreign Application Priority Data

Jun. 21, 2018 (DE) .......................... 102018210076.4

(51) Int. Cl.
*A61M 60/816* (2021.01)
*A61M 60/174* (2021.01)
(Continued)

(52) U.S. Cl.
CPC ........ *A61M 60/816* (2021.01); *A61M 60/174* (2021.01); *A61M 60/178* (2021.01);
(Continued)

(58) Field of Classification Search
CPC .............. A61M 60/816; A61M 60/174; A61M 60/178; A61M 60/216; A61M 60/237;
(Continued)

(56) References Cited

U.S. PATENT DOCUMENTS

| 2,254,698 A | 9/1941 | Hansen, Jr. |
| 2,310,923 A | 2/1943 | Bean |

(Continued)

FOREIGN PATENT DOCUMENTS

| AU | 7993698 | 2/1999 |
| AU | 2002308409 | 12/2005 |

(Continued)

OTHER PUBLICATIONS

Hertz Ph.D. et al., "Ultrasonic Engineering in Heart Diagnosis", The American Journal of Cardiology, Jan. 1967, vol. 19, No. 1, pp. 6-17.
(Continued)

*Primary Examiner* — Mark W. Bockelman
(74) *Attorney, Agent, or Firm* — Knobbe, Martens, Olson & Bear, LLP

(57) ABSTRACT

The invention relates to a method for detecting a state of wear of a cardiac support system. The method comprises a read-in step and a determination step. During the read-in step, a sensor signal (315) representing an operating state of the cardiac support system is read in. During the determination step, a wear signal (325) is determined using the sensor signal (315) and a comparison rule (320). The wear signal (325) represents the wear condition.

19 Claims, 5 Drawing Sheets

(51) Int. Cl.

| | |
|---|---|
| *A61M 60/178* | (2021.01) |
| *A61M 60/216* | (2021.01) |
| *A61M 60/237* | (2021.01) |
| *A61M 60/538* | (2021.01) |
| *A61M 60/546* | (2021.01) |
| *A61M 60/554* | (2021.01) |
| *A61M 60/592* | (2021.01) |
| *A61M 60/857* | (2021.01) |
| *G16H 40/40* | (2018.01) |
| *G16H 40/67* | (2018.01) |
| *G16H 50/70* | (2018.01) |

(52) U.S. Cl.
CPC ........ *A61M 60/216* (2021.01); *A61M 60/237* (2021.01); *A61M 60/538* (2021.01); *A61M 60/546* (2021.01); *A61M 60/554* (2021.01); *A61M 60/592* (2021.01); *A61M 60/857* (2021.01); *G16H 40/40* (2018.01); *G16H 40/67* (2018.01); *G16H 50/70* (2018.01)

(58) Field of Classification Search
CPC .............. A61M 60/538; A61M 60/546; A61M 60/554; A61M 60/592; A61M 60/857; A61M 60/148; A61M 2205/18; A61M 2205/3306; A61M 2205/332; A61M 2205/3331; A61M 2205/3334; A61M 2205/3368; A61M 2205/3375; G16H 40/40; G16H 40/67; G16H 50/70
See application file for complete search history.

(56) References Cited

U.S. PATENT DOCUMENTS

| | | |
|---|---|---|
| 3,085,407 A | 4/1963 | Tomlinson |
| 3,088,323 A | 5/1963 | Welkowitz et al. |
| 3,505,987 A | 4/1970 | Heilman |
| 3,568,659 A | 3/1971 | Karnegis |
| 3,614,181 A | 10/1971 | Meeks |
| 3,747,998 A | 7/1973 | Klein et al. |
| 3,807,813 A | 4/1974 | Milligan |
| 3,995,617 A | 12/1976 | Watkins et al. |
| 4,023,562 A | 5/1977 | Hynecek et al. |
| 4,115,040 A | 9/1978 | Knorr |
| 4,471,252 A | 9/1984 | West |
| 4,522,194 A | 6/1985 | Normann |
| 4,559,952 A | 12/1985 | Angelsen et al. |
| 4,625,712 A | 12/1986 | Wampler |
| 4,643,641 A | 2/1987 | Clausen et al. |
| 4,753,221 A | 6/1988 | Kensey et al. |
| 4,779,614 A | 10/1988 | Moise |
| 4,781,525 A | 11/1988 | Hubbard et al. |
| 4,785,795 A | 11/1988 | Singh et al. |
| 4,817,586 A | 4/1989 | Wampler |
| 4,846,152 A | 7/1989 | Wampler et al. |
| 4,888,011 A | 12/1989 | Kung et al. |
| 4,889,131 A | 12/1989 | Salem et al. |
| 4,895,557 A | 1/1990 | Moise et al. |
| 4,896,754 A | 1/1990 | Carlson et al. |
| 4,902,272 A | 2/1990 | Milder et al. |
| 4,908,012 A | 3/1990 | Moise et al. |
| 4,927,407 A | 5/1990 | Dorman |
| 4,943,275 A | 7/1990 | Stricker |
| 4,944,722 A | 7/1990 | Carriker et al. |
| 4,968,300 A | 11/1990 | Moutafis et al. |
| 4,971,768 A | 11/1990 | Ealba |
| 4,985,014 A | 1/1991 | Orejola |
| 5,044,897 A | 9/1991 | Dorman |
| 5,045,051 A | 9/1991 | Milder et al. |
| 5,061,256 A | 10/1991 | Wampler |
| 5,089,016 A | 2/1992 | Millner et al. |
| 5,090,957 A | 2/1992 | Moutafis et al. |
| 5,112,292 A | 5/1992 | Hwang et al. |
| 5,112,349 A | 5/1992 | Summers et al. |
| 5,116,305 A | 5/1992 | Milder et al. |
| 5,195,877 A | 3/1993 | Kletschka |
| 5,269,811 A | 12/1993 | Hayes |
| 5,289,821 A | 3/1994 | Swartz |
| 5,297,940 A | 3/1994 | Buse |
| 5,313,765 A | 5/1994 | Martin |
| 5,344,443 A | 9/1994 | Palma et al. |
| 5,354,271 A | 10/1994 | Voda |
| 5,376,114 A | 12/1994 | Jarvik |
| 5,399,145 A | 3/1995 | Ito et al. |
| 5,405,383 A | 4/1995 | Barr |
| 5,443,503 A | 8/1995 | Yamane |
| 5,456,715 A | 10/1995 | Liotta |
| 5,527,159 A | 6/1996 | Bozeman, Jr. et al. |
| 5,599,173 A | 2/1997 | Chen et al. |
| 5,613,935 A | 3/1997 | Jarvik |
| 5,676,651 A | 10/1997 | Larson, Jr. et al. |
| 5,695,471 A | 12/1997 | Wampler |
| 5,720,771 A | 2/1998 | Snell |
| 5,746,709 A | 5/1998 | Rom et al. |
| 5,749,855 A | 5/1998 | Reitan |
| 5,752,976 A | 5/1998 | Duffin et al. |
| 5,766,207 A | 6/1998 | Potter et al. |
| 5,827,203 A | 10/1998 | Nita |
| 5,831,365 A | 11/1998 | Keim et al. |
| 5,888,241 A | 3/1999 | Jarvik |
| 5,888,242 A | 3/1999 | Antaki et al. |
| 5,904,646 A | 5/1999 | Jarvik |
| 5,904,708 A | 5/1999 | Goedeke |
| 5,911,685 A | 6/1999 | Siess et al. |
| 5,921,913 A | 7/1999 | Siess |
| 5,964,694 A | 10/1999 | Siess et al. |
| 5,980,465 A | 11/1999 | Elgas |
| 6,001,056 A | 12/1999 | Jassawalla et al. |
| 6,007,478 A | 12/1999 | Siess et al. |
| 6,018,208 A | 1/2000 | Maher et al. |
| 6,024,704 A | 2/2000 | Meador et al. |
| 6,050,975 A | 4/2000 | Poirier |
| 6,053,873 A | 4/2000 | Govari et al. |
| 6,071,093 A | 6/2000 | Hart |
| 6,116,862 A | 9/2000 | Rau et al. |
| 6,123,659 A | 9/2000 | le Blanc et al. |
| 6,135,710 A | 10/2000 | Araki et al. |
| 6,149,405 A | 11/2000 | Abe et al. |
| 6,155,969 A | 12/2000 | Schima et al. |
| 6,158,984 A | 12/2000 | Cao et al. |
| 6,161,838 A | 12/2000 | Balsells |
| 6,176,822 B1 | 1/2001 | Nix et al. |
| 6,176,848 B1 | 1/2001 | Rau et al. |
| 6,183,412 B1 | 2/2001 | Benkowsi et al. |
| 6,185,460 B1 | 2/2001 | Thompson |
| 6,186,665 B1 | 2/2001 | Maher et al. |
| 6,190,324 B1 | 2/2001 | Kieval et al. |
| 6,210,318 B1 | 4/2001 | Lederman |
| 6,217,541 B1 | 4/2001 | Yu |
| 6,220,832 B1 | 4/2001 | Schob |
| 6,227,820 B1 | 5/2001 | Jarvik |
| 6,231,498 B1 | 5/2001 | Pfeiffer et al. |
| 6,245,007 B1 | 6/2001 | Bedingham et al. |
| 6,254,359 B1 | 7/2001 | Aber |
| 6,264,205 B1 | 7/2001 | Balsells |
| 6,264,601 B1 | 7/2001 | Jassawalla et al. |
| 6,264,645 B1 | 7/2001 | Jonkman |
| 6,293,752 B1 | 9/2001 | Clague et al. |
| 6,314,322 B1 | 11/2001 | Rosenberg |
| 6,351,048 B1 | 2/2002 | Schob et al. |
| 6,361,292 B1 | 3/2002 | Chang et al. |
| 6,398,734 B1 | 6/2002 | Cimochowski et al. |
| 6,432,136 B1 | 8/2002 | Weiss et al. |
| 6,438,409 B1 | 8/2002 | Malik et al. |
| 6,445,956 B1 | 9/2002 | Laird et al. |
| 6,447,266 B2 | 9/2002 | Antaki et al. |
| 6,512,949 B1 | 1/2003 | Combs et al. |
| 6,527,698 B1 | 3/2003 | Kung et al. |
| 6,530,876 B1 | 3/2003 | Spence |
| 6,533,716 B1 | 3/2003 | Schmitz-Rode et al. |
| 6,540,658 B1 | 4/2003 | Fasciano et al. |
| 6,540,659 B1 | 4/2003 | Milbocker |
| 6,544,216 B1 | 4/2003 | Sammler et al. |

(56) References Cited

U.S. PATENT DOCUMENTS

| | | |
|---|---|---|
| 6,561,975 B1 | 5/2003 | Pool et al. |
| 6,579,257 B1 | 6/2003 | Elgas et al. |
| 6,592,620 B1 | 7/2003 | Lancisi et al. |
| 6,595,743 B1 | 7/2003 | Kazatchkov et al. |
| 6,602,182 B1 | 8/2003 | Milbocker |
| 6,605,032 B2 | 8/2003 | Benkowsi et al. |
| 6,623,475 B1 | 9/2003 | Siess |
| 6,652,447 B2 | 11/2003 | Benkowsi et al. |
| 6,719,791 B1 | 4/2004 | Nüsser et al. |
| 6,731,976 B2 | 5/2004 | Penn et al. |
| 6,794,789 B2 | 9/2004 | Siess et al. |
| 6,841,910 B2 | 1/2005 | Gery |
| 6,879,126 B2 | 4/2005 | Paden et al. |
| 6,912,423 B2 | 6/2005 | Ley et al. |
| 6,942,611 B2 | 9/2005 | Siess |
| 6,949,066 B2 | 9/2005 | Bearnson et al. |
| 6,969,345 B2 | 11/2005 | Jassawalla et al. |
| 6,984,201 B2 | 1/2006 | Khaghani et al. |
| 7,014,620 B2 | 3/2006 | Kim |
| 7,022,100 B1 | 4/2006 | Aboul-Hosn et al. |
| 7,024,244 B2 | 4/2006 | Muhlenberg et al. |
| 7,027,875 B2 | 4/2006 | Siess et al. |
| 7,011,620 B1 | 5/2006 | Siess |
| 7,070,398 B2 | 7/2006 | Olsen et al. |
| 7,070,555 B2 | 7/2006 | Siess |
| 7,083,588 B1 | 8/2006 | Shmulewitz et al. |
| 7,138,776 B1 | 11/2006 | Gauthier et al. |
| 7,144,364 B2 | 12/2006 | Barbut et al. |
| 7,160,243 B2 | 1/2007 | Medvedev |
| 7,175,588 B2 | 2/2007 | Morello |
| 7,177,681 B2 | 2/2007 | Xhu |
| 7,238,151 B2 | 7/2007 | Frazier |
| 7,241,257 B1 | 7/2007 | Ainsworth et al. |
| 7,264,606 B2 | 9/2007 | Jarvik et al. |
| 7,393,181 B2 | 7/2008 | McBride et al. |
| 7,396,327 B2 | 7/2008 | Morello |
| 7,462,019 B1 | 12/2008 | Allarie et al. |
| 7,479,102 B2 | 1/2009 | Jarvik |
| 7,502,648 B2 | 3/2009 | Okubo et al. |
| 7,513,864 B2 | 4/2009 | Kantrowitz et al. |
| 7,520,850 B2 | 4/2009 | Brockway |
| 7,591,777 B2 | 9/2009 | LaRose |
| 7,736,296 B2 | 6/2010 | Siess et al. |
| 7,744,560 B2 | 6/2010 | Struble |
| 7,762,941 B2 | 7/2010 | Jarvik |
| 7,794,384 B2 | 9/2010 | Sugiura et al. |
| 7,798,952 B2 | 9/2010 | Tansley et al. |
| 7,819,916 B2 | 10/2010 | Yaegashi |
| 7,841,976 B2 | 11/2010 | McBride et al. |
| 7,850,593 B2 | 12/2010 | Vincent et al. |
| 7,850,594 B2 | 12/2010 | Sutton et al. |
| 7,856,335 B2 | 12/2010 | Morello et al. |
| 7,862,501 B2 | 1/2011 | Woodward et al. |
| 7,878,967 B1 | 2/2011 | Khanal |
| 7,934,909 B2 | 2/2011 | Jenson |
| 7,914,436 B1 | 3/2011 | Kung |
| 7,951,062 B2 | 5/2011 | Morello |
| 7,951,129 B2 | 5/2011 | Chinchoy |
| 7,959,551 B2 | 6/2011 | Jarvik |
| 7,963,905 B2 | 6/2011 | Salmonsen et al. |
| 7,988,728 B2 | 8/2011 | Ayre |
| 7,998,190 B2 | 8/2011 | Gharib et al. |
| 8,012,079 B2 | 9/2011 | Delgado, III |
| 8,075,472 B2 | 12/2011 | Zilbershlag et al. |
| 8,088,059 B2 | 1/2012 | Jarvik |
| 8,114,008 B2 | 2/2012 | Hidaka et al. |
| 8,123,669 B2 | 2/2012 | Siess et al. |
| RE43,299 E | 4/2012 | Siess |
| 8,152,845 B2 | 4/2012 | Bourque |
| 8,177,703 B2 | 5/2012 | Smith et al. |
| 8,190,390 B2 | 5/2012 | Morello et al. |
| 8,211,028 B2 | 7/2012 | Karamanoglu et al. |
| 8,216,122 B2 | 7/2012 | Kung |
| 8,303,482 B2 | 11/2012 | Schima et al. |
| 8,323,173 B2 | 12/2012 | Benkowsi et al. |
| 8,371,997 B2 | 2/2013 | Shifflette |
| 8,376,926 B2 | 2/2013 | Benkowsi et al. |
| 8,382,695 B1 | 2/2013 | Patel |
| 8,388,565 B2 | 3/2013 | Shifflette |
| 8,419,609 B2 | 4/2013 | Shambaugh, Jr. et al. |
| 8,435,182 B1 | 5/2013 | Tamura |
| 8,449,443 B2 | 5/2013 | Rodefeld et al. |
| 8,449,444 B2 | 5/2013 | Poirier |
| 8,480,555 B2 | 7/2013 | Kung |
| 8,485,961 B2 | 7/2013 | Campbell et al. |
| 8,512,012 B2 | 8/2013 | Akdis et al. |
| 8,535,211 B2 | 9/2013 | Campbell et al. |
| 8,545,380 B2 | 10/2013 | Farnan et al. |
| 8,562,508 B2 | 10/2013 | Dague et al. |
| 8,585,572 B2 | 11/2013 | Mehmanesh |
| 8,591,393 B2 | 11/2013 | Walters et al. |
| 8,591,538 B2 | 11/2013 | Gellman |
| 8,591,539 B2 | 11/2013 | Gellman |
| 8,594,790 B2 | 11/2013 | Kjellstrom et al. |
| 8,597,170 B2 | 12/2013 | Walters et al. |
| 8,617,239 B2 | 12/2013 | Reitan |
| 8,622,949 B2 | 1/2014 | Zafirelis et al. |
| 8,641,594 B2 | 2/2014 | LaRose et al. |
| 8,657,733 B2 | 2/2014 | Ayre et al. |
| 8,657,875 B2 | 2/2014 | Kung et al. |
| 8,684,362 B2 | 4/2014 | Balsells et al. |
| 8,684,904 B2 | 4/2014 | Campbell et al. |
| 8,690,749 B1 | 4/2014 | Nunez |
| 8,715,151 B2 | 5/2014 | Poirier |
| 8,721,517 B2 | 5/2014 | Zeng et al. |
| 8,727,959 B2 | 5/2014 | Reitan et al. |
| 8,731,664 B2 | 5/2014 | Foster et al. |
| 8,734,331 B2 | 5/2014 | Evans et al. |
| 8,747,293 B2 | 6/2014 | Arndt et al. |
| 8,814,933 B2 | 8/2014 | Siess |
| 8,849,398 B2 | 9/2014 | Evans |
| 8,864,642 B2 | 10/2014 | Scheckel |
| 8,864,643 B2 | 10/2014 | Reichenbach et al. |
| 8,864,644 B2 | 10/2014 | Yomtov |
| 8,876,685 B2 | 11/2014 | Crosby et al. |
| 8,882,477 B2 | 11/2014 | Fritz, IV et al. |
| 8,888,728 B2 | 11/2014 | Aboul-Hosn et al. |
| 8,894,387 B2 | 11/2014 | White |
| 8,897,873 B2 | 11/2014 | Schima et al. |
| 8,900,060 B2 | 12/2014 | Liebing |
| 8,900,115 B2 | 12/2014 | Bolling et al. |
| 8,903,492 B2 | 12/2014 | Soykan et al. |
| 8,932,246 B2 | 1/2015 | Ferrari |
| 8,992,406 B2 | 3/2015 | Corbett |
| 8,992,407 B2 | 3/2015 | Smith et al. |
| 9,028,216 B2 | 5/2015 | Schumacher et al. |
| 9,028,392 B2 | 5/2015 | Shifflette |
| 9,033,863 B2 | 5/2015 | Jarvik |
| 9,091,271 B2 | 7/2015 | Bourque |
| 9,138,518 B2 | 9/2015 | Campbell et al. |
| 9,144,638 B2 | 9/2015 | Zimmermann et al. |
| 9,162,017 B2 | 10/2015 | Evans et al. |
| 9,192,705 B2 | 11/2015 | Yanai et al. |
| 9,199,020 B2 | 12/2015 | Siess |
| 9,265,870 B2 | 2/2016 | Reichenbach et al. |
| 9,297,735 B2 | 3/2016 | Graichen et al. |
| 9,308,305 B2 | 4/2016 | Chen et al. |
| 9,314,556 B2 | 4/2016 | Tuseth |
| 9,327,067 B2 | 5/2016 | Zeng et al. |
| 9,327,068 B2 | 5/2016 | Aboul-Hosn et al. |
| 9,345,824 B2 | 5/2016 | Mohl et al. |
| 9,370,613 B2 | 6/2016 | Hsu et al. |
| 9,371,826 B2 | 6/2016 | Yanai et al. |
| 9,381,286 B2 | 7/2016 | Spence et al. |
| 9,421,311 B2 | 8/2016 | Tanner et al. |
| 9,427,508 B2 | 8/2016 | Reyes et al. |
| 9,433,713 B2 | 9/2016 | Corbett et al. |
| 9,440,013 B2 | 9/2016 | Dowling et al. |
| 9,474,840 B2 | 10/2016 | Siess |
| 9,486,566 B2 | 11/2016 | Siess |
| 9,492,601 B2 | 11/2016 | Casas et al. |
| 9,511,179 B2 | 12/2016 | Casas et al. |
| 9,533,084 B2 | 1/2017 | Siess et al. |
| 9,539,378 B2 | 1/2017 | Tuseth |

(56) References Cited

U.S. PATENT DOCUMENTS

| | | |
|---|---|---|
| 9,550,017 B2 | 1/2017 | Spanier et al. |
| 9,555,173 B2 | 1/2017 | Spanier |
| 9,555,175 B2 | 1/2017 | Bulent et al. |
| 9,556,873 B2 | 1/2017 | Yanai et al. |
| 9,561,313 B2 | 2/2017 | Taskin |
| 9,566,374 B2 | 2/2017 | Spence et al. |
| 9,579,433 B2 | 2/2017 | LaRose et al. |
| 9,585,991 B2 | 3/2017 | Spence |
| 9,592,397 B2 | 3/2017 | Hansen et al. |
| 9,616,157 B2 | 4/2017 | Akdis |
| 9,623,162 B2 | 4/2017 | Graham et al. |
| 9,623,163 B1 | 4/2017 | Fischi |
| 9,636,442 B2 | 5/2017 | Karmon et al. |
| 9,656,010 B2 | 5/2017 | Burke |
| 9,669,142 B2 | 6/2017 | Spanier et al. |
| 9,669,144 B2 | 6/2017 | Spanier et al. |
| 9,675,738 B2 | 6/2017 | Tanner et al. |
| 9,675,739 B2 | 6/2017 | Tanner et al. |
| 9,675,740 B2 | 6/2017 | Zeng et al. |
| 9,682,180 B2 | 6/2017 | Hoarau et al. |
| 9,694,123 B2 | 7/2017 | Bourque et al. |
| 9,713,701 B2 | 7/2017 | Sarkar et al. |
| 9,731,058 B2 | 8/2017 | Siebenhaar et al. |
| 9,744,282 B2 | 8/2017 | Rosenberg et al. |
| 9,759,222 B2 | 9/2017 | Zimmermann et al. |
| 9,770,543 B2 | 9/2017 | Tanner et al. |
| 9,789,238 B2 | 10/2017 | Aboul-Hosn et al. |
| 9,801,990 B2 | 10/2017 | Lynch |
| 9,814,813 B2 | 11/2017 | Corbett |
| 9,821,100 B2 | 11/2017 | Corbett et al. |
| 9,833,550 B2 | 12/2017 | Siess |
| 9,848,899 B2 | 12/2017 | Sliwa et al. |
| 9,849,223 B2 | 12/2017 | LaRose |
| 9,849,224 B2 | 12/2017 | Angwin et al. |
| 9,872,948 B2 | 1/2018 | Siess |
| 9,878,087 B2 | 1/2018 | Richardson et al. |
| 9,907,890 B2 | 3/2018 | Muller |
| 9,919,087 B2 | 3/2018 | Pfeffer et al. |
| 9,943,236 B2 | 4/2018 | Bennett et al. |
| 9,950,101 B2 | 4/2018 | Smith et al. |
| 9,950,102 B2 | 4/2018 | Spence et al. |
| 9,968,719 B2 | 5/2018 | Colella |
| 9,974,894 B2 | 5/2018 | Morello |
| 9,999,714 B2 | 6/2018 | Spanier et al. |
| 10,010,662 B2 | 7/2018 | Wiesener et al. |
| 10,022,480 B2 | 7/2018 | Greatrex et al. |
| 10,029,037 B2 | 7/2018 | Muller et al. |
| 10,052,420 B2 | 8/2018 | Medvedev et al. |
| 10,123,875 B2 | 11/2018 | Wildhirt et al. |
| 10,124,102 B2 | 11/2018 | Bulent et al. |
| 10,130,742 B2 | 11/2018 | Tuseth |
| 10,149,932 B2 | 12/2018 | McBride et al. |
| 10,179,197 B2 | 1/2019 | Kaiser et al. |
| 10,201,645 B2 | 2/2019 | Muller |
| 10,207,038 B2 | 2/2019 | Neumann |
| 10,220,129 B2 | 3/2019 | Ayre et al. |
| 10,232,099 B2 | 3/2019 | Peters et al. |
| 10,238,782 B2 | 3/2019 | Barry |
| 10,238,783 B2 | 3/2019 | Aboul-Hosn et al. |
| 10,251,986 B2 | 4/2019 | Larose et al. |
| 10,279,093 B2 | 5/2019 | Reichenbach et al. |
| 10,293,090 B2 | 5/2019 | Bonde et al. |
| 10,300,185 B2 | 5/2019 | Aboul-Hosn et al. |
| 10,300,249 B2 | 5/2019 | Tao et al. |
| 10,322,217 B2 | 6/2019 | Spence |
| 10,342,906 B2 | 7/2019 | D'Ambrosio et al. |
| 10,350,342 B2 | 7/2019 | Thomas et al. |
| 10,357,598 B2 | 7/2019 | Aboul-Hosn et al. |
| 10,361,617 B2 | 7/2019 | Mueller et al. |
| 10,371,150 B2 | 8/2019 | Wu et al. |
| 10,376,162 B2 | 8/2019 | Edelman et al. |
| 10,413,651 B2 | 9/2019 | Yomtov et al. |
| 10,420,869 B2 | 9/2019 | Cornen |
| 10,426,879 B2 | 10/2019 | Farnan |
| 10,434,232 B2 | 10/2019 | Wu et al. |
| 10,449,275 B2 | 10/2019 | Corbett |
| 10,449,279 B2 | 10/2019 | Muller |
| 10,478,538 B2 | 11/2019 | Scheckel et al. |
| 10,478,539 B2 | 11/2019 | Pfeffer et al. |
| 10,478,542 B2 | 11/2019 | Jahangir |
| 10,500,322 B2 | 12/2019 | Karch |
| 10,500,323 B2 | 12/2019 | Heuring et al. |
| 10,512,537 B2 | 12/2019 | Corbett et al. |
| 10,525,178 B2 | 1/2020 | Zeng |
| 10,537,670 B2 | 1/2020 | Tuseth et al. |
| 10,537,672 B2 | 1/2020 | Tuseth et al. |
| 10,549,020 B2 | 2/2020 | Spence et al. |
| 10,557,475 B2 | 2/2020 | Roehn |
| 10,561,771 B2 | 2/2020 | Heilman et al. |
| 10,561,772 B2 | 2/2020 | Schumacher |
| 10,561,773 B2 | 2/2020 | Ferrari et al. |
| 10,576,191 B2 | 3/2020 | LaRose |
| 10,584,589 B2 | 3/2020 | Schumacher et al. |
| 10,589,012 B2 | 3/2020 | Toellner et al. |
| 10,589,013 B2 | 3/2020 | Bourque |
| 10,610,626 B2 | 4/2020 | Spanier et al. |
| 10,617,808 B2 | 4/2020 | Hastie et al. |
| 10,632,241 B2 | 4/2020 | Schenck et al. |
| 10,660,998 B2 | 5/2020 | Hodges |
| 10,662,967 B2 | 5/2020 | Scheckel |
| 10,668,195 B2 | 6/2020 | Flores |
| 10,669,855 B2 | 6/2020 | Toellner et al. |
| 10,722,631 B2 | 7/2020 | Salahieh et al. |
| 10,732,583 B2 | 8/2020 | Rudser |
| 10,814,053 B2 | 10/2020 | Throckmorton et al. |
| 10,857,273 B2 | 12/2020 | Hodges et al. |
| 10,857,275 B2 | 12/2020 | Granegger |
| 11,027,114 B2 | 6/2021 | D'Ambrosio et al. |
| 11,033,729 B2 | 6/2021 | Scheckel et al. |
| 11,045,638 B2 | 6/2021 | Keenan et al. |
| RE48,649 E | 7/2021 | Siess |
| 11,058,863 B2 | 7/2021 | Demou |
| 11,058,865 B2 | 7/2021 | Fitzgerald et al. |
| 11,065,434 B2 | 7/2021 | Egler et al. |
| 11,067,085 B2 | 7/2021 | Granegger et al. |
| 11,092,158 B2 | 8/2021 | Siess et al. |
| 11,097,092 B2 | 8/2021 | Siess et al. |
| 11,103,689 B2 | 8/2021 | Siess et al. |
| 11,103,690 B2 | 8/2021 | Epple |
| 11,107,626 B2 | 8/2021 | Siess et al. |
| 11,120,908 B2 | 9/2021 | Agnello et al. |
| 11,123,538 B2 | 9/2021 | Epple et al. |
| 11,123,539 B2 | 9/2021 | Pfeffer et al. |
| 11,123,541 B2 | 9/2021 | Corbett et al. |
| 11,129,978 B2 | 9/2021 | Pfeffer et al. |
| 11,131,968 B2 | 9/2021 | Rudser |
| 11,141,579 B2 | 10/2021 | Steingräber |
| 11,147,960 B2 | 10/2021 | Spanier et al. |
| 11,154,701 B2 | 10/2021 | Reyes et al. |
| 11,154,702 B2 | 10/2021 | Kadrolkar et al. |
| 11,160,970 B2 | 11/2021 | Muller et al. |
| 11,167,124 B2 | 11/2021 | Pfeffer et al. |
| 11,173,297 B2 | 11/2021 | Muller |
| 11,179,557 B2 | 11/2021 | Georges et al. |
| 11,185,678 B2 | 11/2021 | Smith et al. |
| 11,185,680 B2 | 11/2021 | Tuval et al. |
| 11,185,682 B2 | 11/2021 | Farnan |
| 11,191,944 B2 | 12/2021 | Tuval et al. |
| 11,191,945 B2 | 12/2021 | Siess et al. |
| 11,197,618 B2 | 12/2021 | Edelman et al. |
| 11,197,989 B2 | 12/2021 | Arslan et al. |
| 11,202,901 B2 | 12/2021 | Barry |
| 11,217,344 B2 | 1/2022 | Agnello |
| 11,219,756 B2 | 1/2022 | Tanner et al. |
| 11,229,786 B2 | 1/2022 | Zeng et al. |
| 11,235,138 B2 | 2/2022 | Gross-Hardt et al. |
| 11,235,139 B2 | 2/2022 | Kudlik |
| 11,235,140 B2 | 2/2022 | Siess et al. |
| 11,241,568 B2 | 2/2022 | Keenan et al. |
| 11,241,569 B2 | 2/2022 | Delgado, III |
| 11,241,572 B2 | 2/2022 | Dague et al. |
| 11,253,693 B2 | 2/2022 | Pfeffer et al. |
| 11,260,212 B2 | 3/2022 | Tuval et al. |
| 11,260,213 B2 | 3/2022 | Zeng et al. |

(56) References Cited

U.S. PATENT DOCUMENTS

| | | |
|---|---|---|
| 11,260,215 B2 | 3/2022 | Scheckel et al. |
| 11,273,299 B2 | 3/2022 | Wolman et al. |
| 11,273,300 B2 | 3/2022 | Schafir |
| 11,273,301 B2 | 3/2022 | Pfeffer et al. |
| 11,278,711 B2 | 3/2022 | Liebing |
| 11,280,345 B2 | 3/2022 | Bredenbreuker et al. |
| 11,285,309 B2 | 3/2022 | Tuval et al. |
| 11,285,310 B2 | 3/2022 | Curran et al. |
| 11,285,311 B2 | 3/2022 | Siess et al. |
| 11,291,824 B2 | 4/2022 | Schwammenthal et al. |
| 11,291,825 B2 | 4/2022 | Tuval et al. |
| 11,291,826 B2 | 4/2022 | Tuval et al. |
| 11,298,519 B2 | 4/2022 | Josephy et al. |
| 11,298,520 B2 | 4/2022 | Schwammenthal et al. |
| 11,298,521 B2 | 4/2022 | Schwammenthal et al. |
| 11,298,523 B2 | 4/2022 | Tuval et al. |
| 11,298,524 B2 | 4/2022 | El Katerji et al. |
| 11,298,525 B2 | 4/2022 | Jahangir |
| 11,305,103 B2 | 4/2022 | Larose et al. |
| 11,305,105 B2 | 4/2022 | Corbett et al. |
| 11,311,711 B2 | 4/2022 | Casas et al. |
| 11,311,712 B2 | 4/2022 | Zeng et al. |
| 11,313,228 B2 | 4/2022 | Schumacher et al. |
| 11,316,679 B2 | 4/2022 | Agnello |
| D951,435 S | 5/2022 | Motomura et al. |
| 11,318,295 B2 | 5/2022 | Reyes et al. |
| 11,320,382 B2 | 5/2022 | Aikawa |
| 11,324,395 B2 | 5/2022 | Banik et al. |
| 11,324,940 B2 | 5/2022 | Earles et al. |
| 11,324,941 B2 | 5/2022 | Xu et al. |
| 11,331,082 B2 | 5/2022 | Itoh et al. |
| 11,331,465 B2 | 5/2022 | Epple |
| 11,331,466 B2 | 5/2022 | Keen et al. |
| 11,331,467 B2 | 5/2022 | King et al. |
| 11,331,470 B2 | 5/2022 | Muller et al. |
| 11,337,724 B2 | 5/2022 | Masubuchi et al. |
| 11,338,124 B2 | 5/2022 | Pfeffer et al. |
| 11,338,125 B2 | 5/2022 | Liu et al. |
| 11,344,716 B2 | 5/2022 | Taskin |
| 11,344,717 B2 | 5/2022 | Kallenbach et al. |
| 11,351,356 B2 | 6/2022 | Mohl |
| 11,351,357 B2 | 6/2022 | Mohl |
| 11,351,358 B2 | 6/2022 | Nix et al. |
| 11,351,359 B2 | 6/2022 | Clifton et al. |
| 11,357,438 B2 | 6/2022 | Stewart et al. |
| 11,357,967 B2 | 6/2022 | Zeng et al. |
| 11,357,968 B2 | 6/2022 | El Katerji et al. |
| 11,364,373 B2 | 6/2022 | Corbett et al. |
| 11,368,081 B2 | 6/2022 | Vogt et al. |
| 11,369,785 B2 | 6/2022 | Callaway et al. |
| 11,369,786 B2 | 6/2022 | Menon et al. |
| 11,376,415 B2 | 7/2022 | Mohl |
| 11,376,419 B2 | 7/2022 | Reyes et al. |
| 11,389,639 B2 | 7/2022 | Casas |
| 11,389,641 B2 | 7/2022 | Nguyen et al. |
| 11,413,443 B2 | 8/2022 | Hodges et al. |
| 11,413,444 B2 | 8/2022 | Nix et al. |
| 11,413,445 B2 | 8/2022 | Brown et al. |
| 11,413,446 B2 | 8/2022 | Siess et al. |
| 11,415,150 B2 | 8/2022 | Richert et al. |
| 11,420,041 B2 | 8/2022 | Karch |
| 11,421,701 B2 | 8/2022 | Schumacher et al. |
| 11,428,236 B2 | 8/2022 | McBride et al. |
| 11,433,168 B2 | 9/2022 | Wu et al. |
| 11,434,921 B2 | 9/2022 | McBride et al. |
| 11,434,922 B2 | 9/2022 | Roehn |
| 11,439,806 B2 | 9/2022 | Kimball et al. |
| 11,446,481 B2 | 9/2022 | Wolman et al. |
| 11,446,482 B2 | 9/2022 | Kirchhoff et al. |
| 11,452,859 B2 | 9/2022 | Earles et al. |
| 11,460,030 B2 | 10/2022 | Shambaugh et al. |
| 11,471,662 B2 | 10/2022 | Akkerman et al. |
| 11,471,663 B2 | 10/2022 | Tuval et al. |
| 11,471,665 B2 | 10/2022 | Clifton et al. |
| 11,478,627 B2 | 10/2022 | Siess et al. |
| 11,478,628 B2 | 10/2022 | Muller et al. |
| 11,478,629 B2 | 10/2022 | Harjes et al. |
| 11,484,698 B2 | 11/2022 | Radman |
| 11,484,699 B2 | 11/2022 | Tuval et al. |
| 11,486,400 B2 | 11/2022 | Schumacher |
| 11,491,320 B2 | 11/2022 | Siess |
| 11,491,322 B2 | 11/2022 | Muller et al. |
| 11,497,896 B2 | 11/2022 | Tanner et al. |
| 11,497,906 B2 | 11/2022 | Grace et al. |
| 11,511,101 B2 | 11/2022 | Hastie et al. |
| 11,511,103 B2 | 11/2022 | Salahieh et al. |
| 11,511,104 B2 | 11/2022 | Dur et al. |
| 11,517,726 B2 | 12/2022 | Siess et al. |
| 11,517,736 B2 | 12/2022 | Earles et al. |
| 11,517,737 B2 | 12/2022 | Struthers et al. |
| 11,517,738 B2 | 12/2022 | Wisniewski |
| 11,517,739 B2 | 12/2022 | Toellner |
| 11,517,740 B2 | 12/2022 | Agarwa et al. |
| 11,521,723 B2 | 12/2022 | Liu et al. |
| 11,524,137 B2 | 12/2022 | Jahangir |
| 11,524,165 B2 | 12/2022 | Tan et al. |
| 11,527,322 B2 | 12/2022 | Agnello et al. |
| 11,529,062 B2 | 12/2022 | Moyer et al. |
| 11,534,596 B2 | 12/2022 | Schafir et al. |
| 11,554,260 B2 | 1/2023 | Reyes et al. |
| 11,565,103 B2 | 1/2023 | Farago et al. |
| 11,569,015 B2 | 1/2023 | Mourran et al. |
| 11,572,879 B2 | 2/2023 | Mohl |
| 11,574,741 B2 | 2/2023 | Tan et al. |
| 11,577,067 B2 | 2/2023 | Breidall et al. |
| 11,577,068 B2 | 2/2023 | Spence et al. |
| 11,581,083 B2 | 2/2023 | El Katerji et al. |
| 11,583,659 B2 | 2/2023 | Pfeffer et al. |
| 11,583,670 B2 | 2/2023 | Pfeifer et al. |
| 11,583,671 B2 | 2/2023 | Nguyen et al. |
| 11,583,672 B2 | 2/2023 | Weber et al. |
| 11,587,337 B2 | 2/2023 | Lemay et al. |
| 11,590,336 B2 | 2/2023 | Harjes et al. |
| 11,590,337 B2 | 2/2023 | Granegger et al. |
| 11,590,338 B2 | 2/2023 | Barry |
| 11,592,028 B2 | 2/2023 | Schumacher et al. |
| 11,596,727 B2 | 3/2023 | Siess et al. |
| 11,602,627 B2 | 3/2023 | Leonhardt |
| 11,617,876 B2 | 4/2023 | Scheckel et al. |
| 11,622,695 B1 | 4/2023 | Adriola et al. |
| 11,628,293 B2 | 4/2023 | Gandhi et al. |
| 11,632,015 B2 | 4/2023 | Sconzert et al. |
| 11,633,586 B2 | 4/2023 | Tanner et al. |
| 11,638,813 B2 | 5/2023 | West |
| 11,639,722 B2 | 5/2023 | Medvedev et al. |
| 11,642,511 B2 | 5/2023 | Delgado, III |
| 11,648,386 B2 | 5/2023 | Poirer |
| 11,648,387 B2 | 5/2023 | Schwammenthal et al. |
| 11,648,388 B2 | 5/2023 | Siess et al. |
| 11,648,389 B2 | 5/2023 | Wang et al. |
| 11,648,390 B2 | 5/2023 | Spanier et al. |
| 11,648,391 B2 | 5/2023 | Schwammenthal et al. |
| 11,648,392 B2 | 5/2023 | Tuval et al. |
| 11,648,393 B2 | 5/2023 | Taskin et al. |
| 11,653,841 B2 | 5/2023 | Reyes et al. |
| 11,654,273 B2 | 5/2023 | Granegger et al. |
| 11,654,275 B2 | 5/2023 | Brandt |
| 11,654,276 B2 | 5/2023 | Fitzgerald et al. |
| 11,660,441 B2 | 5/2023 | Fitzgerald et al. |
| 11,666,746 B2 | 6/2023 | Ferrari et al. |
| 11,666,747 B2 | 6/2023 | Tuval et al. |
| 11,666,748 B2 | 6/2023 | Kronstedt et al. |
| 11,668,321 B2 | 6/2023 | Richert et al. |
| 11,674,517 B2 | 6/2023 | Mohl |
| 11,676,718 B2 | 6/2023 | Agnello et al. |
| 11,679,234 B2 | 6/2023 | King et al. |
| 11,679,249 B2 | 6/2023 | Scheckel et al. |
| 11,684,275 B2 | 6/2023 | Tuval et al. |
| 11,684,276 B2 | 6/2023 | Cros et al. |
| 11,684,769 B2 | 6/2023 | Harjes et al. |
| 11,690,521 B2 | 7/2023 | Tuval et al. |
| 11,690,996 B2 | 7/2023 | Siess et al. |
| 11,694,539 B2 | 7/2023 | Kudlik et al. |
| 11,694,813 B2 | 7/2023 | El Katerji et al. |

(56) References Cited

U.S. PATENT DOCUMENTS

| | | |
|---|---|---|
| 11,696,782 B2 | 7/2023 | Carlson et al. |
| 11,697,016 B2 | 7/2023 | Epple |
| 11,701,510 B2 | 7/2023 | Demou |
| 11,702,938 B2 | 7/2023 | Schumacher et al. |
| 11,703,064 B2 | 7/2023 | Bredenbreuker et al. |
| 11,707,617 B2 | 7/2023 | Reyes et al. |
| 11,708,833 B2 | 7/2023 | McBride et al. |
| 11,712,167 B2 | 8/2023 | Medvedev et al. |
| 11,744,987 B2 | 9/2023 | Siess et al. |
| 11,745,005 B2 | 9/2023 | Delgado, III |
| 11,746,906 B1 | 9/2023 | Balta et al. |
| 11,752,322 B2 | 9/2023 | Aboulhosn et al. |
| 11,752,323 B2 | 9/2023 | Edwards et al. |
| 11,754,075 B2 | 9/2023 | Schuelke et al. |
| 11,754,077 B1 | 9/2023 | Mohl |
| 11,759,612 B2 | 9/2023 | Tanner et al. |
| 11,759,622 B2 | 9/2023 | Siess et al. |
| 11,766,555 B2 | 9/2023 | Matthes et al. |
| D1,001,145 S | 10/2023 | Lussier et al. |
| D1,001,146 S | 10/2023 | Lussier et al. |
| 11,771,884 B2 | 10/2023 | Siess et al. |
| 11,771,885 B2 | 10/2023 | Liu et al. |
| 11,779,234 B2 | 10/2023 | Harjes et al. |
| 11,779,751 B2 | 10/2023 | Earles et al. |
| 11,781,551 B2 | 10/2023 | Yanai et al. |
| 11,786,386 B2 | 10/2023 | Brady et al. |
| 11,786,700 B2 | 10/2023 | Pfeffer et al. |
| 11,786,720 B2 | 10/2023 | Muller |
| 11,790,487 B2 | 10/2023 | Barbato et al. |
| 11,793,994 B2 | 10/2023 | Josephy et al. |
| 11,804,767 B2 | 10/2023 | Vogt et al. |
| 11,806,116 B2 | 11/2023 | Tuval et al. |
| 11,806,117 B2 | 11/2023 | Tuval et al. |
| 11,806,517 B2 | 11/2023 | Petersen |
| 11,806,518 B2 | 11/2023 | Michelena et al. |
| 11,813,079 B2 | 11/2023 | Lau et al. |
| 11,813,443 B2 | 11/2023 | Hanson et al. |
| 11,813,444 B2 | 11/2023 | Siess et al. |
| 11,818,782 B2 | 11/2023 | Doudian et al. |
| 11,819,678 B2 | 11/2023 | Siess et al. |
| 11,824,381 B2 | 11/2023 | Conyers et al. |
| 11,826,127 B2 | 11/2023 | Casas |
| 11,832,793 B2 | 12/2023 | McWeeney et al. |
| 11,832,868 B2 | 12/2023 | Smail et al. |
| 11,833,278 B2 | 12/2023 | Siess et al. |
| 11,833,342 B2 | 12/2023 | Tanner et al. |
| 11,837,364 B2 | 12/2023 | Lee et al. |
| 11,839,754 B2 | 12/2023 | Tuval et al. |
| 11,844,592 B2 | 12/2023 | Tuval et al. |
| 11,844,940 B2 | 12/2023 | D'Ambrosio et al. |
| 11,850,073 B2 | 12/2023 | Wright et al. |
| 11,850,412 B2 | 12/2023 | Grauwinkel et al. |
| 11,850,413 B2 | 12/2023 | Zeng et al. |
| 11,850,414 B2 | 12/2023 | Schenck et al. |
| 11,850,415 B2 | 12/2023 | Schwammenthal et al. |
| D1,012,284 S | 1/2024 | Glaser et al. |
| 11,857,345 B2 | 1/2024 | Hanson et al. |
| 11,857,743 B2 | 1/2024 | Fantuzzi et al. |
| 11,857,777 B2 | 1/2024 | Earles et al. |
| 11,864,878 B2 | 1/2024 | Duval et al. |
| 11,865,238 B2 | 1/2024 | Siess et al. |
| 11,872,384 B2 | 1/2024 | Cotter |
| 11,883,005 B2 | 1/2024 | Golden et al. |
| 11,883,207 B2 | 1/2024 | El Katerji et al. |
| 11,883,310 B2 | 1/2024 | Nolan et al. |
| 11,883,641 B2 | 1/2024 | Dur et al. |
| D1,014,552 S | 2/2024 | Lussier et al. |
| 11,890,082 B2 | 2/2024 | Cros et al. |
| 11,890,212 B2 | 2/2024 | Gilmartin et al. |
| 11,896,199 B2 | 2/2024 | Lent et al. |
| 11,896,482 B2 | 2/2024 | Delaloye et al. |
| 11,898,642 B2 | 2/2024 | Stanton et al. |
| 11,900,660 B2 | 2/2024 | Saito et al. |
| 11,903,657 B2 | 2/2024 | Geric et al. |
| 11,904,104 B2 | 2/2024 | Jahangir |
| 11,906,411 B2 | 2/2024 | Graichen et al. |
| 11,911,550 B2 | 2/2024 | Itamochi et al. |
| 11,911,579 B2 | 2/2024 | Tanner et al. |
| D1,017,634 S | 3/2024 | Lussier et al. |
| D1,017,699 S | 3/2024 | Moore et al. |
| 11,918,470 B2 | 3/2024 | Jarral et al. |
| 11,918,496 B2 | 3/2024 | Folan |
| 11,918,726 B2 | 3/2024 | Siess et al. |
| 11,918,800 B2 | 3/2024 | Muller et al. |
| 11,923,078 B2 | 3/2024 | Fallen et al. |
| 11,923,093 B2 | 3/2024 | Moffitt et al. |
| 11,925,356 B2 | 3/2024 | Anderson et al. |
| 11,925,570 B2 | 3/2024 | Lydecker et al. |
| 11,925,794 B2 | 3/2024 | Malkin et al. |
| 11,925,795 B2 | 3/2024 | Muller et al. |
| 11,925,796 B2 | 3/2024 | Tanner et al. |
| 11,925,797 B2 | 3/2024 | Tanner et al. |
| 11,931,073 B2 | 3/2024 | Walsh et al. |
| 11,931,528 B2 | 3/2024 | Rohl et al. |
| 11,931,588 B2 | 3/2024 | Aghassian |
| 11,938,311 B2 | 3/2024 | Corbett et al. |
| 11,944,805 B2 | 4/2024 | Stotz |
| 11,980,385 B2 | 5/2024 | Haselman |
| 11,986,274 B2 | 5/2024 | Edelman |
| 11,986,604 B2 | 5/2024 | Siess |
| 12,005,248 B2 | 6/2024 | Vogt et al. |
| 2001/0009645 A1 | 7/2001 | Noda |
| 2001/0016686 A1 | 8/2001 | Okada et al. |
| 2001/0037093 A1 | 11/2001 | Benkowski et al. |
| 2001/0039828 A1 | 11/2001 | Shin et al. |
| 2001/0041934 A1 | 11/2001 | Yamazaki et al. |
| 2002/0076322 A1 | 6/2002 | Maeda et al. |
| 2002/0147495 A1 | 10/2002 | Petroff |
| 2002/0151761 A1 | 10/2002 | Viole et al. |
| 2002/0153664 A1 | 10/2002 | Schroeder |
| 2003/0060685 A1 | 3/2003 | Houser |
| 2003/0069465 A1 | 4/2003 | Benkowski et al. |
| 2003/0091450 A1 | 5/2003 | Davis et al. |
| 2003/0100816 A1 | 5/2003 | Siess |
| 2003/0111800 A1 | 6/2003 | Kreutzer |
| 2003/0130581 A1 | 7/2003 | Salo et al. |
| 2003/0139643 A1 | 7/2003 | Smith et al. |
| 2003/0167002 A1 | 9/2003 | Nagar et al. |
| 2003/0191357 A1 | 10/2003 | Frazier |
| 2004/0022640 A1 | 2/2004 | Siess et al. |
| 2004/0044266 A1 | 3/2004 | Siess et al. |
| 2004/0065143 A1 | 4/2004 | Husher |
| 2004/0066107 A1 | 4/2004 | Gery |
| 2004/0102674 A1 | 5/2004 | Zadini et al. |
| 2004/0115038 A1 | 6/2004 | Nuesser et al. |
| 2004/0167376 A1 | 8/2004 | Peters et al. |
| 2004/0167410 A1 | 8/2004 | Hettrick |
| 2004/0225177 A1 | 11/2004 | Coleman et al. |
| 2004/0234391 A1 | 11/2004 | Izraelev |
| 2004/0241019 A1 | 12/2004 | Goldowsky |
| 2004/0260346 A1 | 12/2004 | Overall et al. |
| 2005/0006083 A1 | 1/2005 | Chen et al. |
| 2005/0019167 A1 | 1/2005 | Nusser et al. |
| 2005/0085683 A1 | 4/2005 | Bolling et al. |
| 2005/0107658 A1 | 5/2005 | Brockway |
| 2005/0126268 A1 | 6/2005 | Ouriev et al. |
| 2005/0220636 A1 | 10/2005 | Henein et al. |
| 2005/0267322 A1 | 12/2005 | LaRose |
| 2006/0030809 A1 | 2/2006 | Barzilay et al. |
| 2006/0062672 A1 | 3/2006 | McBride et al. |
| 2006/0108901 A1 | 5/2006 | Mao-Chin |
| 2006/0122583 A1 | 6/2006 | Pesach et al. |
| 2006/0155158 A1 | 7/2006 | Aboul-Hosn |
| 2006/0196277 A1 | 9/2006 | Allen et al. |
| 2006/0224110 A1 | 10/2006 | Scott et al. |
| 2006/0229488 A1 | 10/2006 | Ayre et al. |
| 2006/0276682 A1 | 12/2006 | Bolling et al. |
| 2006/0287600 A1 | 12/2006 | McEowen |
| 2006/0287604 A1 | 12/2006 | Hickey |
| 2007/0004959 A1 | 1/2007 | Carrier et al. |
| 2007/0060787 A1 | 3/2007 | Peters et al. |
| 2007/0073352 A1 | 3/2007 | Euler et al. |
| 2007/0088214 A1 | 4/2007 | Shuros et al. |
| 2007/0142696 A1 | 6/2007 | Crosby et al. |

(56) References Cited

U.S. PATENT DOCUMENTS

| | | |
|---|---|---|
| 2007/0156006 A1 | 7/2007 | Smith et al. |
| 2007/0255352 A1 | 11/2007 | Roline et al. |
| 2007/0266778 A1 | 11/2007 | Corey et al. |
| 2007/0282209 A1 | 12/2007 | Lui et al. |
| 2008/0015517 A1 | 1/2008 | Geistert et al. |
| 2008/0058925 A1 | 3/2008 | Cohen |
| 2008/0082005 A1 | 4/2008 | Stern et al. |
| 2008/0086027 A1 | 4/2008 | Siess et al. |
| 2008/0091239 A1 | 4/2008 | Johansson et al. |
| 2008/0097595 A1 | 4/2008 | Gabbay |
| 2008/0102096 A1 | 5/2008 | Molin et al. |
| 2008/0108901 A1 | 5/2008 | Baba et al. |
| 2008/0108930 A1 | 5/2008 | Weitzel et al. |
| 2008/0114339 A1 | 5/2008 | McBride et al. |
| 2008/0133006 A1 | 6/2008 | Crosby et al. |
| 2008/0146996 A1 | 6/2008 | Smisson |
| 2008/0210016 A1 | 9/2008 | Zwirn et al. |
| 2008/0262289 A1 | 10/2008 | Goldowsky |
| 2008/0262361 A1 | 10/2008 | Gutfinger et al. |
| 2008/0269822 A1 | 10/2008 | Ljungstrom et al. |
| 2008/0275339 A1 | 11/2008 | Thiemann et al. |
| 2008/0292478 A1 | 11/2008 | Baykut et al. |
| 2008/0306328 A1 | 12/2008 | Ercolani |
| 2009/0004037 A1 | 1/2009 | Ito |
| 2009/0024042 A1 | 1/2009 | Nunez et al. |
| 2009/0025459 A1 | 1/2009 | Zhang et al. |
| 2009/0064755 A1 | 3/2009 | Fleischli et al. |
| 2009/0105799 A1 | 4/2009 | Hekmat et al. |
| 2009/0112312 A1 | 4/2009 | Larose et al. |
| 2009/0131765 A1 | 5/2009 | Roschak et al. |
| 2009/0138080 A1 | 5/2009 | Siess et al. |
| 2009/0203957 A1 | 8/2009 | LaRose et al. |
| 2009/0204163 A1 | 8/2009 | Shuros et al. |
| 2009/0204205 A1 | 8/2009 | Larose et al. |
| 2009/0226328 A1 | 9/2009 | Morello |
| 2009/0312650 A1 | 12/2009 | Maile et al. |
| 2010/0010354 A1 | 1/2010 | Skerl et al. |
| 2010/0041939 A1 | 2/2010 | Siess |
| 2010/0082099 A1 | 4/2010 | Vodermayer et al. |
| 2010/0087742 A1 | 4/2010 | Bishop et al. |
| 2010/0160801 A1 | 6/2010 | Takatani et al. |
| 2010/0191035 A1 | 7/2010 | Kang et al. |
| 2010/0219967 A1 | 9/2010 | Kaufmann |
| 2010/0222632 A1 | 9/2010 | Poirier |
| 2010/0222633 A1 | 9/2010 | Poirier |
| 2010/0222635 A1 | 9/2010 | Poirier |
| 2010/0222878 A1 | 9/2010 | Poirier |
| 2010/0268017 A1 | 10/2010 | Siess |
| 2010/0298625 A1 | 11/2010 | Reichenbach et al. |
| 2010/0324378 A1 | 12/2010 | Tran et al. |
| 2011/0004075 A1 | 1/2011 | Stahmann et al. |
| 2011/0022057 A1 | 1/2011 | Eigler et al. |
| 2011/0071336 A1 | 3/2011 | Yomtov |
| 2011/0144744 A1 | 6/2011 | Wampler |
| 2011/0184224 A1 | 7/2011 | Garrigue |
| 2011/0184301 A1 | 7/2011 | Holmstrom |
| 2011/0218435 A1 | 9/2011 | Srinivasan et al. |
| 2011/0230821 A1 | 9/2011 | Babic |
| 2011/0237863 A1 | 9/2011 | Ricci et al. |
| 2011/0238172 A1 | 9/2011 | Akdis |
| 2012/0022645 A1 | 1/2012 | Burke |
| 2012/0035645 A1 | 2/2012 | Gross |
| 2012/0084024 A1 | 4/2012 | Norcross, Jr. |
| 2012/0088954 A1 | 4/2012 | Foster |
| 2012/0093628 A1 | 4/2012 | Liebing |
| 2012/0134793 A1 | 5/2012 | Wu et al. |
| 2012/0150089 A1 | 6/2012 | Penka et al. |
| 2012/0172655 A1 | 7/2012 | Campbell et al. |
| 2012/0178986 A1 | 7/2012 | Campbell et al. |
| 2012/0203476 A1 | 8/2012 | Dam |
| 2012/0247200 A1 | 10/2012 | Ahonen et al. |
| 2012/0283506 A1 | 11/2012 | Meister et al. |
| 2012/0310036 A1 | 12/2012 | Peters et al. |
| 2012/0310037 A1 | 12/2012 | Choi et al. |
| 2012/0330214 A1 | 12/2012 | Peters et al. |
| 2013/0041204 A1 | 2/2013 | Heilman et al. |
| 2013/0046129 A1 | 2/2013 | Medvedev et al. |
| 2013/0053623 A1 | 2/2013 | Evans |
| 2013/0066141 A1 | 3/2013 | Doerr et al. |
| 2013/0072846 A1 | 3/2013 | Heide et al. |
| 2013/0085318 A1 | 4/2013 | Toellner |
| 2013/0116575 A1 | 5/2013 | Mickle et al. |
| 2013/0144379 A1 | 6/2013 | Najafi et al. |
| 2013/0209292 A1 | 8/2013 | Baykut et al. |
| 2013/0281761 A1 | 10/2013 | Kapur |
| 2013/0289376 A1 | 10/2013 | Lang |
| 2013/0303830 A1 | 11/2013 | Zeng et al. |
| 2013/0303831 A1 | 11/2013 | Evans |
| 2013/0303832 A1 | 11/2013 | Wampler |
| 2013/0330219 A1 | 12/2013 | LaRose et al. |
| 2014/0005467 A1 | 1/2014 | Farnan et al. |
| 2014/0013852 A1 | 1/2014 | Brown et al. |
| 2014/0051908 A1 | 2/2014 | Khanal et al. |
| 2014/0079557 A1 | 3/2014 | LaRose et al. |
| 2014/0100414 A1 | 4/2014 | Tamez et al. |
| 2014/0107399 A1 | 4/2014 | Spence |
| 2014/0114202 A1 | 4/2014 | Hein et al. |
| 2014/0128659 A1 | 5/2014 | Heuring et al. |
| 2014/0167545 A1 | 6/2014 | Bremner et al. |
| 2014/0194717 A1 | 7/2014 | Wildhirt et al. |
| 2014/0200389 A1 | 7/2014 | Yanai et al. |
| 2014/0207232 A1 | 7/2014 | Garrigue |
| 2014/0243688 A1 | 8/2014 | Caron et al. |
| 2014/0275720 A1 | 9/2014 | Ferrari |
| 2014/0275721 A1 | 9/2014 | Yanai et al. |
| 2014/0296677 A1 | 10/2014 | McEowen |
| 2014/0303426 A1 | 10/2014 | Kerkhoffs et al. |
| 2014/0330069 A1 | 11/2014 | Hastings et al. |
| 2014/0341726 A1 | 11/2014 | Wu et al. |
| 2015/0031936 A1 | 1/2015 | LaRose et al. |
| 2015/0032007 A1 | 1/2015 | Ottevanger et al. |
| 2015/0051435 A1 | 2/2015 | Siess et al. |
| 2015/0051438 A1 | 2/2015 | Taskin |
| 2015/0099923 A1 | 4/2015 | Magovern et al. |
| 2015/0141832 A1 | 5/2015 | Yu et al. |
| 2015/0141842 A1 | 5/2015 | Spanier et al. |
| 2015/0157216 A1 | 6/2015 | Stigall et al. |
| 2015/0171694 A1 | 6/2015 | Dallas |
| 2015/0174307 A1 | 6/2015 | Eckman et al. |
| 2015/0190092 A1 | 7/2015 | Mori |
| 2015/0250935 A1 | 9/2015 | Anderson et al. |
| 2015/0273184 A1 | 10/2015 | Scott et al. |
| 2015/0290372 A1 | 10/2015 | Muller et al. |
| 2015/0290373 A1 | 10/2015 | Rudser et al. |
| 2015/0306290 A1 | 10/2015 | Rosenberg et al. |
| 2015/0306291 A1 | 10/2015 | Bonde et al. |
| 2015/0327921 A1 | 11/2015 | Govari |
| 2015/0335804 A1 | 11/2015 | Marseille et al. |
| 2015/0343179 A1 | 12/2015 | Schumacher et al. |
| 2015/0365738 A1 | 12/2015 | Purvis et al. |
| 2016/0000983 A1 | 1/2016 | Mohl et al. |
| 2016/0008531 A1 | 1/2016 | Wang et al. |
| 2016/0022889 A1 | 1/2016 | Bluvshtein et al. |
| 2016/0022890 A1 | 1/2016 | Schwammenthal et al. |
| 2016/0030649 A1 | 2/2016 | Zeng |
| 2016/0038663 A1 | 2/2016 | Taskin et al. |
| 2016/0045165 A1 | 2/2016 | Braido et al. |
| 2016/0045654 A1 | 2/2016 | Connor |
| 2016/0095968 A1 | 4/2016 | Rudser |
| 2016/0101230 A1 | 4/2016 | Ochsner et al. |
| 2016/0144089 A1 | 5/2016 | Woo et al. |
| 2016/0144166 A1 | 5/2016 | Decréet al. |
| 2016/0166747 A1 | 6/2016 | Frazier et al. |
| 2016/0213828 A1 | 7/2016 | Sievers |
| 2016/0223086 A1 | 8/2016 | Balsells et al. |
| 2016/0250399 A1 | 9/2016 | Tiller et al. |
| 2016/0278856 A1 | 9/2016 | Panescu |
| 2016/0279311 A1 | 9/2016 | Cecere et al. |
| 2016/0338629 A1 | 11/2016 | Doerr |
| 2016/0367739 A1 | 12/2016 | Wiesener et al. |
| 2016/0375187 A1 | 12/2016 | Lee et al. |
| 2017/0010144 A1 | 1/2017 | Lenner et al. |
| 2017/0021069 A1 | 1/2017 | Hodges |
| 2017/0021070 A1 | 1/2017 | Petersen |

(56) References Cited

U.S. PATENT DOCUMENTS

| | | |
|---|---|---|
| 2017/0021074 A1 | 1/2017 | Opfermann et al. |
| 2017/0035952 A1 | 2/2017 | Muller |
| 2017/0049945 A1 | 2/2017 | Halvorsen et al. |
| 2017/0049947 A1 | 2/2017 | Corbett et al. |
| 2017/0080136 A1 | 3/2017 | Janeczek et al. |
| 2017/0086780 A1 | 3/2017 | Sokulin et al. |
| 2017/0087286 A1 | 3/2017 | Spanier et al. |
| 2017/0087288 A1 | 3/2017 | Groß-HardTim et al. |
| 2017/0112985 A1 | 4/2017 | Yomtov |
| 2017/0128644 A1 | 5/2017 | Foster |
| 2017/0128646 A1 | 5/2017 | Karch |
| 2017/0136164 A1 | 5/2017 | Yeatts |
| 2017/0136225 A1 | 5/2017 | Siess et al. |
| 2017/0143952 A1 | 5/2017 | Siess et al. |
| 2017/0157309 A1 | 6/2017 | Begg et al. |
| 2017/0202575 A1 | 7/2017 | Stanfield et al. |
| 2017/0209633 A1 | 7/2017 | Cohen |
| 2017/0224279 A1 | 8/2017 | Cahan et al. |
| 2017/0239407 A1 | 8/2017 | Hayward |
| 2017/0258980 A1 | 9/2017 | Katsuki et al. |
| 2017/0274128 A1 | 9/2017 | Tamburino et al. |
| 2017/0333607 A1 | 11/2017 | Zarins |
| 2017/0333608 A1 | 11/2017 | Zeng |
| 2017/0340787 A1 | 11/2017 | Corbett et al. |
| 2017/0340788 A1 | 11/2017 | Korakianitis et al. |
| 2017/0340789 A1 | 11/2017 | Bonde et al. |
| 2017/0343043 A1 | 11/2017 | Walsh et al. |
| 2017/0348470 A1 | 12/2017 | D'Ambrosio et al. |
| 2017/0354812 A1 | 12/2017 | Callaghan et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0050141 A1 | 2/2018 | Corbett et al. |
| 2018/0055979 A1 | 3/2018 | Corbett et al. |
| 2018/0064860 A1 | 3/2018 | Nunez et al. |
| 2018/0078159 A1 | 3/2018 | Edelman et al. |
| 2018/0093070 A1 | 4/2018 | Cottone |
| 2018/0099076 A1 | 4/2018 | LaRose |
| 2018/0110907 A1 | 4/2018 | Keenan et al. |
| 2018/0110910 A1 | 4/2018 | Rodemerk et al. |
| 2018/0133379 A1 | 5/2018 | Farnan et al. |
| 2018/0154058 A1 | 6/2018 | Menon et al. |
| 2018/0169312 A1 | 6/2018 | Barry |
| 2018/0169313 A1 | 6/2018 | Schwammenthal et al. |
| 2018/0207336 A1 | 7/2018 | Solem |
| 2018/0221551 A1 | 8/2018 | Tanner et al. |
| 2018/0221553 A1 | 8/2018 | Taskin |
| 2018/0228950 A1 | 8/2018 | Janeczek et al. |
| 2018/0228953 A1 | 8/2018 | Siess et al. |
| 2018/0243004 A1 | 8/2018 | von Segesser et al. |
| 2018/0243489 A1 | 8/2018 | Haddadi |
| 2018/0250456 A1 | 9/2018 | Nitzan et al. |
| 2018/0250457 A1 | 9/2018 | Morello et al. |
| 2018/0256796 A1 | 9/2018 | Hansen |
| 2018/0256797 A1 | 9/2018 | Schenck et al. |
| 2018/0256800 A1 | 9/2018 | Conyers et al. |
| 2018/0264182 A1 | 9/2018 | Spanier et al. |
| 2018/0280598 A1 | 10/2018 | Curran et al. |
| 2018/0289877 A1 | 10/2018 | Schumacher et al. |
| 2018/0303990 A1 | 10/2018 | Siess et al. |
| 2018/0311423 A1 | 11/2018 | Zeng et al. |
| 2018/0316209 A1 | 11/2018 | Gliner |
| 2018/0318483 A1 | 11/2018 | Dague et al. |
| 2018/0318547 A1 | 11/2018 | Yokoyama |
| 2018/0326131 A1 | 11/2018 | Muller et al. |
| 2018/0326132 A1 | 11/2018 | Maimon et al. |
| 2018/0335037 A1 | 11/2018 | Shambaugh et al. |
| 2018/0345028 A1 | 12/2018 | Aboud et al. |
| 2018/0353667 A1 | 12/2018 | Moyer et al. |
| 2018/0361042 A1 | 12/2018 | Fitzgerald et al. |
| 2018/0369469 A1 | 12/2018 | Le Duc De Lillers et al. |
| 2019/0001034 A1 | 1/2019 | Taskin et al. |
| 2019/0001038 A1 | 1/2019 | Yomtov et al. |
| 2019/0004037 A1 | 1/2019 | Zhang et al. |
| 2019/0030228 A1 | 1/2019 | Keenan et al. |
| 2019/0046702 A1 | 2/2019 | Siess et al. |
| 2019/0046703 A1 | 2/2019 | Shambaugh et al. |
| 2019/0054223 A1 | 2/2019 | Frazier et al. |
| 2019/0060539 A1 | 2/2019 | Siess et al. |
| 2019/0060543 A1 | 2/2019 | Khanal et al. |
| 2019/0076167 A1 | 3/2019 | Fantuzzi et al. |
| 2019/0083690 A1 | 3/2019 | Siess et al. |
| 2019/0099532 A1 | 4/2019 | Er |
| 2019/0101130 A1 | 4/2019 | Bredenbreuker et al. |
| 2019/0105437 A1 | 4/2019 | Siess et al. |
| 2019/0117865 A1 | 4/2019 | Walters et al. |
| 2019/0125948 A1 | 5/2019 | Stanfield et al. |
| 2019/0143016 A1 | 5/2019 | Corbett et al. |
| 2019/0143018 A1 | 5/2019 | Salahieh et al. |
| 2019/0154053 A1 | 5/2019 | McBride et al. |
| 2019/0167122 A1 | 6/2019 | Obermiller et al. |
| 2019/0167875 A1 | 6/2019 | Simon et al. |
| 2019/0167878 A1 | 6/2019 | Rowe |
| 2019/0170153 A1 | 6/2019 | Scheckel |
| 2019/0175806 A1 | 6/2019 | Tuval et al. |
| 2019/0184078 A1 | 6/2019 | Zilbershlag et al. |
| 2019/0184080 A1 | 6/2019 | Mohl |
| 2019/0192752 A1 | 6/2019 | Tiller et al. |
| 2019/0192753 A1 | 6/2019 | Liu et al. |
| 2019/0201603 A1 | 7/2019 | Siess et al. |
| 2019/0209755 A1 | 7/2019 | Nix et al. |
| 2019/0209758 A1 | 7/2019 | Tuval et al. |
| 2019/0211836 A1 | 7/2019 | Schumacher et al. |
| 2019/0211846 A1 | 7/2019 | Liebing |
| 2019/0216995 A1 | 7/2019 | Kapur et al. |
| 2019/0217002 A1 | 7/2019 | Urakabe |
| 2019/0223877 A1 | 7/2019 | Nitzen et al. |
| 2019/0240680 A1 | 8/2019 | Hayakawa |
| 2019/0254543 A1 | 8/2019 | Hartholt et al. |
| 2019/0269840 A1 | 9/2019 | Tuval et al. |
| 2019/0275224 A1 | 9/2019 | Hanson et al. |
| 2019/0282741 A1 | 9/2019 | Franano et al. |
| 2019/0282744 A1 | 9/2019 | D'Ambrosio et al. |
| 2019/0290817 A1 | 9/2019 | Guo et al. |
| 2019/0298902 A1 | 10/2019 | Siess et al. |
| 2019/0316591 A1 | 10/2019 | Toellner |
| 2019/0321527 A1 | 10/2019 | King et al. |
| 2019/0321529 A1 | 10/2019 | Korakianitis et al. |
| 2019/0321531 A1 | 10/2019 | Cambronne et al. |
| 2019/0336664 A1 | 11/2019 | Liebing |
| 2019/0344000 A1 | 11/2019 | Kushwaha et al. |
| 2019/0344001 A1 | 11/2019 | Salahieh et al. |
| 2019/0351117 A1 | 11/2019 | Cambronne et al. |
| 2019/0351118 A1 | 11/2019 | Graichen et al. |
| 2019/0351119 A1 | 11/2019 | Cambronne et al. |
| 2019/0351120 A1 | 11/2019 | Kushwaha et al. |
| 2019/0358378 A1 | 11/2019 | Schumacher |
| 2019/0358379 A1 | 11/2019 | Wiessler et al. |
| 2019/0358384 A1 | 11/2019 | Epple |
| 2019/0365975 A1 | 12/2019 | Muller et al. |
| 2019/0383298 A1 | 12/2019 | Toellner |
| 2020/0016309 A1 | 1/2020 | Kallenbach et al. |
| 2020/0023109 A1 | 1/2020 | Epple |
| 2020/0030507 A1 | 1/2020 | Higgins et al. |
| 2020/0030509 A1 | 1/2020 | Siess et al. |
| 2020/0030510 A1 | 1/2020 | Higgins |
| 2020/0030511 A1 | 1/2020 | Higgins |
| 2020/0030512 A1 | 1/2020 | Higgins et al. |
| 2020/0038567 A1 | 2/2020 | Siess et al. |
| 2020/0038568 A1 | 2/2020 | Higgins et al. |
| 2020/0038571 A1 | 2/2020 | Jahangir |
| 2020/0060559 A1 | 2/2020 | Edelman et al. |
| 2020/0069857 A1 | 3/2020 | Schwammenthal et al. |
| 2020/0088207 A1 | 3/2020 | Schumacher et al. |
| 2020/0114053 A1 | 4/2020 | Salahieh et al. |
| 2020/0129684 A1 | 4/2020 | Pfeffer et al. |
| 2020/0139028 A1 | 5/2020 | Scheckel et al. |
| 2020/0139029 A1 | 5/2020 | Scheckel et al. |
| 2020/0147283 A1 | 5/2020 | Tanner et al. |
| 2020/0164125 A1 | 5/2020 | Muller et al. |
| 2020/0164126 A1 | 5/2020 | Muller |
| 2020/0253583 A1 | 8/2020 | Brisken et al. |
| 2020/0312450 A1 | 10/2020 | Agnello et al. |
| 2020/0345337 A1 | 11/2020 | Muller et al. |

(56) References Cited

U.S. PATENT DOCUMENTS

| | | |
|---|---|---|
| 2020/0350812 A1 | 11/2020 | Vogt et al. |
| 2021/0052793 A1 | 2/2021 | Struthers et al. |
| 2021/0236803 A1 | 8/2021 | Stotz |
| 2021/0268264 A1 | 9/2021 | Stotz |
| 2021/0290087 A1 | 9/2021 | Schlebusch |
| 2021/0290929 A1 | 9/2021 | Stotz |
| 2021/0290930 A1 | 9/2021 | Kasel |
| 2021/0290932 A1 | 9/2021 | Stotz |
| 2021/0290933 A1 | 9/2021 | Stotz |
| 2021/0290937 A1 | 9/2021 | Baumbach |
| 2021/0313869 A1 | 10/2021 | Strasswiemer et al. |
| 2021/0316133 A1 | 10/2021 | Kassel et al. |
| 2021/0322756 A1 | 10/2021 | Vollmer et al. |
| 2021/0330958 A1 | 10/2021 | Stotz et al. |
| 2021/0338999 A1 | 11/2021 | Stotz et al. |
| 2021/0339002 A1 | 11/2021 | Schlebusch et al. |
| 2021/0339004 A1 | 11/2021 | Schlebusch et al. |
| 2021/0339005 A1 | 11/2021 | Stotz et al. |
| 2021/0346674 A1 | 11/2021 | Baumbach et al. |
| 2021/0346675 A1 | 11/2021 | Schlebusch et al. |
| 2021/0346676 A1 | 11/2021 | Schlebusch et al. |
| 2021/0346677 A1 | 11/2021 | Baumbach et al. |
| 2021/0346680 A1 | 11/2021 | Vogt et al. |
| 2021/0378523 A1 | 12/2021 | Budde |
| 2021/0379352 A1 | 12/2021 | Schlebusch et al. |
| 2021/0379355 A1 | 12/2021 | Schuelke et al. |
| 2021/0379358 A1 | 12/2021 | Schuelke et al. |
| 2021/0379359 A1 | 12/2021 | Schellenberg |
| 2021/0379360 A1 | 12/2021 | Schellenberg |
| 2021/0384812 A1 | 12/2021 | Vollmer et al. |
| 2021/0393944 A1 | 12/2021 | Wenning |
| 2022/0008714 A1 | 1/2022 | Stotz |
| 2022/0016411 A1 | 1/2022 | Winterwerber |
| 2022/0032032 A1 | 2/2022 | Schlebusch et al. |
| 2022/0032036 A1 | 2/2022 | Baumbach et al. |
| 2022/0039669 A1 | 2/2022 | Schlebusch et al. |
| 2022/0047173 A1 | 2/2022 | Stotz et al. |
| 2022/0050037 A1 | 2/2022 | Stotz et al. |
| 2022/0072296 A1 | 3/2022 | Mori |
| 2022/0072297 A1 | 3/2022 | Tuval et al. |
| 2022/0072298 A1 | 3/2022 | Spanier et al. |
| 2022/0076807 A1 | 3/2022 | Agnello |
| 2022/0079457 A1 | 3/2022 | Tuval et al. |
| 2022/0080178 A1 | 3/2022 | Salahieh et al. |
| 2022/0080180 A1 | 3/2022 | Siess et al. |
| 2022/0080182 A1 | 3/2022 | Earles et al. |
| 2022/0080183 A1 | 3/2022 | Earles et al. |
| 2022/0080184 A1 | 3/2022 | Clifton et al. |
| 2022/0080185 A1 | 3/2022 | Clifton et al. |
| 2022/0105337 A1 | 4/2022 | Salahieh et al. |
| 2022/0105339 A1 | 4/2022 | Nix et al. |
| 2022/0126083 A1 | 4/2022 | Grauwinkel et al. |
| 2022/0126085 A1 | 4/2022 | Farnan |
| 2022/0126086 A1 | 4/2022 | Schlebusch et al. |
| 2022/0142462 A1 | 5/2022 | Douk et al. |
| 2022/0161018 A1 | 5/2022 | Mitze et al. |
| 2022/0161019 A1 | 5/2022 | Mitze et al. |
| 2022/0161021 A1 | 5/2022 | Mitze et al. |
| 2022/0241580 A1 | 8/2022 | Stotz et al. |
| 2022/0407403 A1 | 12/2022 | Vogt et al. |
| 2023/0001178 A1 | 1/2023 | Corbett et al. |
| 2023/0173250 A1 | 6/2023 | Stigloher |
| 2023/0191141 A1 | 6/2023 | Wenning et al. |
| 2023/0277833 A1 | 9/2023 | Sharma et al. |
| 2023/0277836 A1 | 9/2023 | Schellenberg et al. |
| 2023/0293878 A1 | 9/2023 | Christof et al. |
| 2023/0364411 A1 | 11/2023 | Bette |
| 2024/0011808 A1 | 1/2024 | Winzer et al. |
| 2024/0074828 A1 | 3/2024 | Wenning |
| 2024/0075277 A1 | 3/2024 | Schellenberg |
| 2024/0102475 A1 | 3/2024 | Schuelke et al. |

FOREIGN PATENT DOCUMENTS

| | | |
|---|---|---|
| AU | 2012261669 | 1/2013 |
| AU | 2013203301 | 5/2013 |
| AU | 2013273663 | 1/2014 |
| BR | PI0904483-3 | 7/2011 |
| CA | 2 026 692 | 4/1992 |
| CA | 2 026 693 | 4/1992 |
| CA | 2 664 835 | 2/2008 |
| CA | 2 796 357 | 10/2011 |
| CA | 3 122 415 | 7/2020 |
| CA | 2 947 984 | 11/2022 |
| CN | 1192351 A | 9/1998 |
| CN | 1222862 A | 7/1999 |
| CN | 1254598 A | 5/2000 |
| CN | 1376523 A | 10/2002 |
| CN | 2535055 | 2/2003 |
| CN | 1118304 C | 8/2003 |
| CN | 2616217 | 5/2004 |
| CN | 1202871 C | 5/2005 |
| CN | 1661338 A | 8/2005 |
| CN | 1833736 A | 9/2006 |
| CN | 200977306 | 11/2007 |
| CN | 101112628 | 1/2008 |
| CN | 101128168 | 2/2008 |
| CN | 101208045 | 6/2008 |
| CN | 101214158 | 7/2008 |
| CN | 201150675 | 11/2008 |
| CN | 101351237 | 1/2009 |
| CN | 101448535 | 6/2009 |
| CN | 101460094 | 6/2009 |
| CN | 101579233 | 11/2009 |
| CN | 201437016 | 4/2010 |
| CN | 101711683 | 5/2010 |
| CN | 201618200 | 11/2010 |
| CN | 201658687 | 12/2010 |
| CN | 201710717 | 1/2011 |
| CN | 201894758 | 7/2011 |
| CN | 102421372 | 4/2012 |
| CN | 102475923 | 5/2012 |
| CN | 102545538 | 7/2012 |
| CN | 202314596 | 7/2012 |
| CN | 102743801 | 10/2012 |
| CN | 102803923 | 11/2012 |
| CN | 103143072 | 6/2013 |
| CN | 103328018 | 9/2013 |
| CN | 103845766 | 6/2014 |
| CN | 103857326 | 6/2014 |
| CN | 103861162 | 6/2014 |
| CN | 103957957 | 7/2014 |
| CN | 203842087 | 9/2014 |
| CN | 104105449 | 10/2014 |
| CN | 104188687 | 12/2014 |
| CN | 104208763 | 12/2014 |
| CN | 104208764 | 12/2014 |
| CN | 203971004 | 12/2014 |
| CN | 104274873 | 1/2015 |
| CN | 204106671 | 1/2015 |
| CN | 204219479 | 3/2015 |
| CN | 103877630 | 2/2016 |
| CN | 205215814 | 5/2016 |
| CN | 103977464 | 8/2016 |
| CN | 104162192 | 9/2016 |
| CN | 106104229 | 11/2016 |
| CN | 106333707 | 1/2017 |
| CN | 104888293 | 3/2017 |
| CN | 106512117 | 3/2017 |
| CN | 206007680 | 3/2017 |
| CN | 104225696 | 6/2017 |
| CN | 107019824 | 8/2017 |
| CN | 206443963 | 8/2017 |
| CN | 107281567 | 10/2017 |
| CN | 104707194 | 11/2017 |
| CN | 107530479 | 1/2018 |
| CN | 107632167 | 1/2018 |
| CN | 107921187 | 4/2018 |
| CN | 105498002 | 6/2018 |
| CN | 106310410 | 7/2018 |
| CN | 109939282 | 6/2019 |

(56) References Cited

FOREIGN PATENT DOCUMENTS

| | | |
|---|---|---|
| CN | 106902404 | 8/2019 |
| CN | 209790495 | 12/2019 |
| CN | 110665079 | 1/2020 |
| CN | 210020563 | 2/2020 |
| CN | 111166948 | 5/2020 |
| CN | 111166949 | 5/2020 |
| DE | 1 001 642 | 1/1957 |
| DE | 1 165 144 | 3/1964 |
| DE | 26 24 058 | 12/1977 |
| DE | 3 545 214 | 7/1986 |
| DE | 195 20 920 | 12/1995 |
| DE | 195 46 336 | 5/1997 |
| DE | 695 01 834 | 10/1998 |
| DE | 198 54 724 | 5/1999 |
| DE | 198 21 307 | 10/1999 |
| DE | 199 10 872 | 10/1999 |
| DE | 199 56 380 | 11/1999 |
| DE | 100 59 714 | 5/2002 |
| DE | 100 60 275 | 6/2002 |
| DE | 101 55 011 | 11/2005 |
| DE | 601 19 592 | 9/2006 |
| DE | 20 2005 020 288 | 6/2007 |
| DE | 10 2006 001 180 | 9/2007 |
| DE | 10 2008 060 357 | 6/2010 |
| DE | 10 2009 007 216 | 8/2010 |
| DE | 10 2009 011 726 | 9/2010 |
| DE | 10 2009 025 464 | 1/2011 |
| DE | 10 2009 039 658 | 3/2011 |
| DE | 10 2009 047 845 | 3/2011 |
| DE | 20 2009 018 416 | 8/2011 |
| DE | 10 2011 106 142 | 12/2012 |
| DE | 20 2011 110 389 | 9/2013 |
| DE | 10 2012 022 456 | 5/2014 |
| DE | 10 2013 007 562 | 11/2014 |
| DE | 10 2015 004 177 | 10/2015 |
| DE | 10 2014 210 299 | 12/2015 |
| DE | 10 2014 212 323 | 12/2015 |
| DE | 11 2014 001 418 | 12/2015 |
| DE | 10 2014 224 151 | 6/2016 |
| DE | 20 2015 009 422 | 7/2017 |
| DE | 10 2012 207 042 | 9/2017 |
| DE | 10 2016 013 334 | 4/2018 |
| DE | 10 2017 212 193 | 1/2019 |
| DE | 10 2018 207 611 | 11/2019 |
| DE | 10 2018 208 945 | 12/2019 |
| DE | 10 2018 211 327 | 1/2020 |
| DE | 10 2018 212 153 | 1/2020 |
| DE | 10 2018 213 350 | 2/2020 |
| DE | 11 2020 003 063 | 3/2022 |
| DE | 11 2020 003 151 | 3/2022 |
| DE | 11 2020 004 148 | 6/2022 |
| EP | 0 050 814 | 5/1982 |
| EP | 0 629 412 | 12/1994 |
| EP | 0 764 448 | 3/1997 |
| EP | 0 794 411 | 9/1997 |
| EP | 0 855 515 | 7/1998 |
| EP | 0 890 179 | 1/1999 |
| EP | 0 916 359 | 5/1999 |
| EP | 1 013 294 | 6/2000 |
| EP | 1 062 959 | 12/2000 |
| EP | 1 339 443 | 11/2001 |
| EP | 1 186 873 | 3/2002 |
| EP | 1 011 803 | 9/2004 |
| EP | 1 475 880 | 11/2004 |
| EP | 1 169 072 | 5/2005 |
| EP | 1 176 999 | 7/2005 |
| EP | 1 354 606 | 6/2006 |
| EP | 1 801 420 | 6/2007 |
| EP | 2 009 233 | 12/2008 |
| EP | 2 098 746 | 9/2009 |
| EP | 2 143 385 | 1/2010 |
| EP | 2 175 770 | 4/2010 |
| EP | 2 403 109 | 1/2012 |
| EP | 2 187 807 | 6/2012 |
| EP | 2 570 143 | 3/2013 |
| EP | 2 401 003 | 10/2013 |
| EP | 3 326 567 | 10/2014 |
| EP | 1 871 441 | 11/2014 |
| EP | 1 898 971 | 3/2015 |
| EP | 2 859 911 | 4/2015 |
| EP | 2 519 273 | 8/2015 |
| EP | 2 438 936 | 10/2015 |
| EP | 2 438 937 | 10/2015 |
| EP | 2 960 515 | 12/2015 |
| EP | 2 968 718 | 1/2016 |
| EP | 1 996 252 | 5/2016 |
| EP | 2 475 415 | 6/2016 |
| EP | 2 906 265 | 7/2016 |
| EP | 2 213 227 | 8/2016 |
| EP | 2 835 141 | 8/2016 |
| EP | 3 069 739 | 9/2016 |
| EP | 3 088 016 | 11/2016 |
| EP | 3 127 562 | 2/2017 |
| EP | 2 585 129 | 3/2017 |
| EP | 3 222 301 | 9/2017 |
| EP | 3 222 302 | 9/2017 |
| EP | 2 945 661 | 11/2017 |
| EP | 2 136 861 | 12/2017 |
| EP | 3 020 426 | 12/2017 |
| EP | 3 038 669 | 1/2018 |
| EP | 3 062 730 | 1/2018 |
| EP | 3 180 050 | 2/2018 |
| EP | 3 287 154 | 2/2018 |
| EP | 1 789 129 | 6/2018 |
| EP | 2 366 412 | 8/2018 |
| EP | 3 205 359 | 8/2018 |
| EP | 3 205 360 | 8/2018 |
| EP | 3 456 367 | 3/2019 |
| EP | 3 119 451 | 6/2019 |
| EP | 3 389 738 | 8/2019 |
| EP | 3 542 835 | 9/2019 |
| EP | 3 542 836 | 9/2019 |
| EP | 3 062 877 | 12/2019 |
| EP | 3 668 560 | 6/2020 |
| EP | 3 711 785 | 9/2020 |
| EP | 3 711 786 | 9/2020 |
| EP | 3 711 787 | 9/2020 |
| EP | 3 142 722 | 12/2020 |
| EP | 3 579 894 | 12/2020 |
| EP | 3 753 594 | 12/2020 |
| EP | 3 188 769 | 1/2021 |
| EP | 3 357 523 | 1/2021 |
| EP | 3 490 122 | 1/2021 |
| EP | 2 869 866 | 2/2021 |
| EP | 3 398 626 | 2/2021 |
| EP | 3 487 549 | 2/2021 |
| EP | 3 490 628 | 2/2021 |
| EP | 3 113 806 | 3/2021 |
| EP | 3 487 548 | 3/2021 |
| EP | 3 509 661 | 3/2021 |
| EP | 3 515 523 | 3/2021 |
| EP | 3 528 863 | 3/2021 |
| EP | 3 615 103 | 3/2021 |
| EP | 4 271 461 | 3/2021 |
| EP | 2 344 218 | 4/2021 |
| EP | 3 436 104 | 4/2021 |
| EP | 3 749 383 | 4/2021 |
| EP | 3 131 600 | 6/2021 |
| EP | 3 131 615 | 6/2021 |
| EP | 3 338 825 | 6/2021 |
| EP | 3 432 944 | 6/2021 |
| EP | 3 684 439 | 7/2021 |
| EP | 2 582 414 | 8/2021 |
| EP | 3 407 930 | 8/2021 |
| EP | 3 782 665 | 8/2021 |
| EP | 3 782 666 | 8/2021 |
| EP | 3 782 668 | 8/2021 |
| EP | 3 858 397 | 8/2021 |
| EP | 3 216 467 | 9/2021 |
| EP | 3 463 505 | 9/2021 |
| EP | 3 884 968 | 9/2021 |
| EP | 3 884 969 | 9/2021 |
| EP | 3 884 970 | 9/2021 |
| EP | 2 599 510 | 10/2021 |

(56) References Cited

FOREIGN PATENT DOCUMENTS

| | | |
|---|---|---|
| EP | 3 003 421 | 10/2021 |
| EP | 3 027 241 | 10/2021 |
| EP | 3 668 561 | 10/2021 |
| EP | 3 579 904 | 11/2021 |
| EP | 2 628 493 | 12/2021 |
| EP | 3 164 168 | 12/2021 |
| EP | 3 344 129 | 12/2021 |
| EP | 3 556 409 | 1/2022 |
| EP | 3 624 868 | 1/2022 |
| EP | 3 624 867 | 3/2022 |
| EP | 3 651 822 | 3/2022 |
| EP | 3 689 389 | 3/2022 |
| EP | 3 697 464 | 3/2022 |
| EP | 3 737 436 | 3/2022 |
| EP | 3 972 661 | 3/2022 |
| EP | 2 967 630 | 4/2022 |
| EP | 3 142 721 | 4/2022 |
| EP | 3 520 834 | 4/2022 |
| EP | 3 586 887 | 4/2022 |
| EP | 3 638 336 | 4/2022 |
| EP | 3 689 388 | 4/2022 |
| EP | 3 765 110 | 4/2022 |
| EP | 3 782 667 | 4/2022 |
| EP | 3 829 673 | 4/2022 |
| EP | 3 976 129 | 4/2022 |
| EP | 3 984 589 | 4/2022 |
| EP | 3 986 528 | 4/2022 |
| EP | 3 649 926 | 5/2022 |
| EP | 3 653 113 | 5/2022 |
| EP | 3 654 006 | 5/2022 |
| EP | 3 735 280 | 5/2022 |
| EP | 3 897 814 | 5/2022 |
| EP | 3 219 339 | 6/2022 |
| EP | 3 737 310 | 7/2022 |
| EP | 2 999 400 | 8/2022 |
| EP | 3 711 788 | 8/2022 |
| EP | 3 899 994 | 8/2022 |
| EP | 3 487 550 | 9/2022 |
| EP | 3 606 575 | 9/2022 |
| EP | 3 694 573 | 9/2022 |
| EP | 3 834 876 | 9/2022 |
| EP | 3 000 492 | 10/2022 |
| EP | 3 600 477 | 10/2022 |
| EP | 3 897 768 | 10/2022 |
| EP | 3 914 310 | 10/2022 |
| EP | 3 914 311 | 10/2022 |
| EP | 3 000 493 | 11/2022 |
| EP | 3 858 422 | 11/2022 |
| EP | 3 866 876 | 11/2022 |
| EP | 3 941 546 | 11/2022 |
| EP | 2 892 583 | 1/2023 |
| EP | 3 370 797 | 1/2023 |
| EP | 3 393 542 | 1/2023 |
| EP | 3 597 231 | 1/2023 |
| EP | 3 656 292 | 1/2023 |
| EP | 3 668 562 | 1/2023 |
| EP | 3 768 345 | 1/2023 |
| EP | 3 856 275 | 1/2023 |
| EP | 2 868 332 | 2/2023 |
| EP | 3 003 420 | 2/2023 |
| EP | 3 397 299 | 2/2023 |
| EP | 3 539 585 | 2/2023 |
| EP | 3 956 010 | 2/2023 |
| EP | 3 046 594 | 3/2023 |
| EP | 3 127 563 | 3/2023 |
| EP | 3 256 186 | 3/2023 |
| EP | 3 288 609 | 3/2023 |
| EP | 3 538 173 | 3/2023 |
| EP | 3 606 576 | 3/2023 |
| EP | 3 927 390 | 3/2023 |
| EP | 3 384 940 | 4/2023 |
| EP | 3 441 616 | 4/2023 |
| EP | 3 938 005 | 4/2023 |
| EP | 3 946 511 | 4/2023 |
| EP | 3 685 562 | 5/2023 |
| EP | 3 544 649 | 6/2023 |
| EP | 3 634 528 | 6/2023 |
| EP | 3 397 298 | 7/2023 |
| EP | 3 809 959 | 7/2023 |
| EP | 3 912 673 | 7/2023 |
| EP | 2 072 150 | 9/2023 |
| EP | 2 961 984 | 9/2023 |
| EP | 3 352 808 | 9/2023 |
| EP | 3 768 156 | 9/2023 |
| EP | 3 554 576 | 10/2023 |
| EP | 3 737 435 | 10/2023 |
| EP | 3 795 208 | 10/2023 |
| EP | 4 052 754 | 10/2023 |
| EP | 4 149 606 | 10/2023 |
| EP | 3 157 596 | 11/2023 |
| EP | 3 515 525 | 11/2023 |
| EP | 3 621 669 | 11/2023 |
| EP | 3 744 362 | 11/2023 |
| EP | 3 766 428 | 11/2023 |
| EP | 3 781 027 | 11/2023 |
| EP | 3 808 390 | 11/2023 |
| EP | 4 061 470 | 11/2023 |
| EP | 4 070 720 | 11/2023 |
| EP | 3 449 958 | 12/2023 |
| EP | 3 687 596 | 12/2023 |
| EP | 3 710 076 | 12/2023 |
| EP | 3 768 340 | 12/2023 |
| EP | 3 787 707 | 12/2023 |
| EP | 3 926 194 | 12/2023 |
| EP | 3 784 305 | 1/2024 |
| EP | 3 801 675 | 1/2024 |
| EP | 3 925 659 | 1/2024 |
| EP | 4 115 919 | 1/2024 |
| EP | 3 566 636 | 2/2024 |
| EP | 3 634 526 | 2/2024 |
| EP | 3 768 342 | 2/2024 |
| EP | 3 768 347 | 2/2024 |
| EP | 3 769 799 | 2/2024 |
| EP | 3 790 606 | 2/2024 |
| EP | 3 930 780 | 2/2024 |
| EP | 3 397 147 | 3/2024 |
| EP | 3 782 695 | 3/2024 |
| EP | 3 854 448 | 3/2024 |
| EP | 4 140 532 | 5/2024 |
| ES | 2 913 485 | 6/2022 |
| FR | 1458525 | 3/1966 |
| GB | 0 648 739 | 1/1951 |
| GB | 2 213 541 | 8/1989 |
| GB | 2 345 387 | 7/2000 |
| GB | 2 451 161 | 12/2011 |
| GB | 2 545 062 | 6/2017 |
| GB | 2 545 750 | 6/2017 |
| JP | S59-080229 | 5/1984 |
| JP | 59-119788 | 8/1984 |
| JP | S61-500059 | 1/1986 |
| JP | S61-125329 | 6/1986 |
| JP | S62-113555 | 7/1987 |
| JP | S62-204733 | 9/1987 |
| JP | S62-282284 | 12/1987 |
| JP | S64-68236 | 3/1989 |
| JP | H02-055886 | 2/1990 |
| JP | 2-79738 | 3/1990 |
| JP | H02-234750 | 9/1990 |
| JP | H04-176471 | 6/1992 |
| JP | H04-108384 | 9/1992 |
| JP | H05-079875 | 3/1993 |
| JP | H06-218044 | 8/1994 |
| JP | H07-047025 | 5/1995 |
| JP | H08-057042 | 3/1996 |
| JP | H08-066398 | 3/1996 |
| JP | H08-327527 | 12/1996 |
| JP | H10-052489 | 2/1998 |
| JP | H10-505766 | 6/1998 |
| JP | 2888609 | 5/1999 |
| JP | 2889384 | 5/1999 |
| JP | H11-239617 | 9/1999 |
| JP | 2000-512191 | 9/2000 |
| JP | 2001-037728 | 2/2001 |
| JP | 2001-506140 | 5/2001 |

(56) References Cited

FOREIGN PATENT DOCUMENTS

| | | |
|---|---|---|
| JP | 2001-515375 | 9/2001 |
| JP | 2001-276213 | 10/2001 |
| JP | 2002-525175 | 8/2002 |
| JP | 2003-019197 | 1/2003 |
| JP | 2003-047656 | 2/2003 |
| JP | 2003-062065 | 3/2003 |
| JP | 2004-515278 | 5/2004 |
| JP | 2004-278375 | 10/2004 |
| JP | 2005-028137 | 2/2005 |
| JP | 2005-507039 | 3/2005 |
| JP | 2005-192687 | 7/2005 |
| JP | 2006-528006 | 12/2006 |
| JP | 2007-222644 | 9/2007 |
| JP | 2008-511414 | 4/2008 |
| JP | 2008-516654 | 5/2008 |
| JP | 2006-518249 | 8/2008 |
| JP | 2008-178690 | 8/2008 |
| JP | 2009-504290 | 2/2009 |
| JP | 2009-240348 | 10/2009 |
| JP | 2010-518907 | 6/2010 |
| JP | 2010-258181 | 11/2010 |
| JP | 2010-534080 | 11/2010 |
| JP | 2012-520157 | 9/2012 |
| JP | 2013-013216 | 1/2013 |
| JP | 2013-519497 | 5/2013 |
| JP | 2013-128792 | 7/2013 |
| JP | 2014-004303 | 1/2014 |
| JP | 2014-524274 | 9/2014 |
| JP | 2015-514529 | 5/2015 |
| JP | 2015-514531 | 5/2015 |
| JP | 2015-515429 | 5/2015 |
| JP | 2015-122448 | 7/2015 |
| JP | 2015-527172 | 9/2015 |
| JP | 2015-181800 | 10/2015 |
| JP | 2016-002466 | 1/2016 |
| JP | 2016-509950 | 4/2016 |
| JP | 2016-532500 | 10/2016 |
| JP | 2017-500932 | 1/2017 |
| JP | 6063151 | 1/2017 |
| JP | 2017-176719 | 10/2017 |
| JP | 2017-532084 | 11/2017 |
| JP | 6267625 | 1/2018 |
| JP | 2018-057878 | 4/2018 |
| JP | 2019-523110 | 8/2019 |
| JP | 6572056 | 9/2019 |
| JP | 2020-072985 | 5/2020 |
| JP | 2018-510708 | 3/2021 |
| KR | 10-2011-0098192 | 9/2011 |
| RO | 131676 | 2/2017 |
| RU | 2 051 695 | 1/1996 |
| TW | 374317 | 11/1999 |
| UA | 97202 C2 | 1/2012 |
| WO | WO 92/015239 | 9/1992 |
| WO | WO 94/009835 | 5/1994 |
| WO | WO 97/037696 | 10/1997 |
| WO | WO 97/039785 | 10/1997 |
| WO | WO 98/043688 | 10/1998 |
| WO | WO 99/049912 | 10/1999 |
| WO | WO 00/033047 | 6/2000 |
| WO | WO 00/033446 | 6/2000 |
| WO | WO 02/022200 | 3/2002 |
| WO | WO 02/041935 | 5/2002 |
| WO | WO 02/070039 | 9/2002 |
| WO | WO 03/075981 | 9/2003 |
| WO | WO 03/103745 | 12/2003 |
| WO | WO 2005/020848 | 3/2005 |
| WO | WO 2005/028014 | 3/2005 |
| WO | WO 2005/037345 | 4/2005 |
| WO | WO 2007/033933 | 3/2007 |
| WO | WO 2007/105842 | 9/2007 |
| WO | WO 2008/017289 | 2/2008 |
| WO | WO 2008/081783 | 7/2008 |
| WO | WO 2009/010888 | 1/2009 |
| WO | WO 2009/046789 | 4/2009 |
| WO | WO 2009/046790 | 4/2009 |
| WO | WO 2009/073037 | 6/2009 |
| WO | WO 2010/119267 | 10/2010 |
| WO | WO 2010/142286 | 12/2010 |
| WO | WO 2010/143272 | 12/2010 |
| WO | WO 2011/003043 | 1/2011 |
| WO | WO 2011/081626 | 7/2011 |
| WO | WO 2011/160858 | 12/2011 |
| WO | WO 2012/018917 | 2/2012 |
| WO | WO 2012/047540 | 4/2012 |
| WO | WO 2012/112129 | 8/2012 |
| WO | WO 2012/112378 | 8/2012 |
| WO | WO 2013/037380 | 3/2013 |
| WO | WO 2013/120957 | 8/2013 |
| WO | WO 2013/160443 | 10/2013 |
| WO | WO 2013/167432 | 11/2013 |
| WO | WO 2013/173239 | 11/2013 |
| WO | WO 2014/042925 | 3/2014 |
| WO | WO 2014/141284 | 9/2014 |
| WO | WO 2014/165635 | 10/2014 |
| WO | WO 2015/039605 | 3/2015 |
| WO | WO 2015/063281 | 5/2015 |
| WO | WO 2015/085076 | 6/2015 |
| WO | WO 2015/085220 | 6/2015 |
| WO | WO 2015/109028 | 7/2015 |
| WO | WO 2015/172173 | 11/2015 |
| WO | WO 2015/175718 | 11/2015 |
| WO | WO 2016/001284 | 1/2016 |
| WO | WO 2016/028644 | 2/2016 |
| WO | WO 2016/066180 | 5/2016 |
| WO | WO 2016/137743 | 9/2016 |
| WO | WO 2016/146661 | 9/2016 |
| WO | WO 2016/146663 | 9/2016 |
| WO | WO 2017/004175 | 1/2017 |
| WO | WO 2017/015764 | 2/2017 |
| WO | WO 2017/021465 | 2/2017 |
| WO | WO 2017/032751 | 3/2017 |
| WO | WO 2017/053988 | 3/2017 |
| WO | WO 2017/060257 | 4/2017 |
| WO | WO 2017/066257 | 4/2017 |
| WO | WO 2017/106190 | 6/2017 |
| WO | WO 2017/112695 | 6/2017 |
| WO | WO 2017/112698 | 6/2017 |
| WO | WO 2017/147291 | 8/2017 |
| WO | WO 2017/159849 | 9/2017 |
| WO | WO 2017/162619 | 9/2017 |
| WO | WO 2017/205909 | 12/2017 |
| WO | WO 2017/214118 | 12/2017 |
| WO | WO 2018/007120 | 1/2018 |
| WO | WO 2018/036927 | 3/2018 |
| WO | WO 2018/048800 | 3/2018 |
| WO | WO 2018/088939 | 3/2018 |
| WO | WO 2018/089970 | 5/2018 |
| WO | WO 2018/109038 | 6/2018 |
| WO | WO 2018/139508 | 8/2018 |
| WO | WO 2018/197306 | 11/2018 |
| WO | WO 2018/213089 | 11/2018 |
| WO | WO 2019/013794 | 1/2019 |
| WO | WO 2019/034670 | 2/2019 |
| WO | WO 2019/034775 | 2/2019 |
| WO | WO 2019/035804 | 2/2019 |
| WO | WO 2019/038343 | 2/2019 |
| WO | WO 2019/057636 | 3/2019 |
| WO | WO 2019/078723 | 4/2019 |
| WO | WO 2019/135767 | 7/2019 |
| WO | WO 2019/137911 | 7/2019 |
| WO | WO 2019/138350 | 7/2019 |
| WO | WO 2019/145253 | 8/2019 |
| WO | WO 2019/158996 | 8/2019 |
| WO | WO 2019/161245 | 8/2019 |
| WO | WO 2019/180104 | 9/2019 |
| WO | WO 2019/180179 | 9/2019 |
| WO | WO 2019/180181 | 9/2019 |
| WO | WO 2019/193604 | 10/2019 |
| WO | WO 2018/135477 | 11/2019 |
| WO | WO 2018/135478 | 11/2019 |
| WO | WO 2019/211410 | 11/2019 |
| WO | WO 2019/219868 | 11/2019 |
| WO | WO 2019/219871 | 11/2019 |
| WO | WO 2019/219872 | 11/2019 |

(56) References Cited

FOREIGN PATENT DOCUMENTS

| | | |
|---|---|---|
| WO | WO 2019/219874 | 11/2019 |
| WO | WO 2019/219876 | 11/2019 |
| WO | WO 2019/219881 | 11/2019 |
| WO | WO 2019/219882 | 11/2019 |
| WO | WO 2019/219883 | 11/2019 |
| WO | WO 2019/219884 | 11/2019 |
| WO | WO 2019/219885 | 11/2019 |
| WO | WO 2019/229210 | 12/2019 |
| WO | WO 2019/229211 | 12/2019 |
| WO | WO 2019/229214 | 12/2019 |
| WO | WO 2019/229220 | 12/2019 |
| WO | WO 2019/229221 | 12/2019 |
| WO | WO 2019/229222 | 12/2019 |
| WO | WO 2019/229223 | 12/2019 |
| WO | WO 2019/234145 | 12/2019 |
| WO | WO 2019/234146 | 12/2019 |
| WO | WO 2019/234148 | 12/2019 |
| WO | WO 2019/234149 | 12/2019 |
| WO | WO 2019/234151 | 12/2019 |
| WO | WO 2019/234152 | 12/2019 |
| WO | WO 2019/234153 | 12/2019 |
| WO | WO 2019/234161 | 12/2019 |
| WO | WO 2019/234162 | 12/2019 |
| WO | WO 2019/234163 | 12/2019 |
| WO | WO 2019/234164 | 12/2019 |
| WO | WO 2019/234166 | 12/2019 |
| WO | WO 2019/234167 | 12/2019 |
| WO | WO 2019/234169 | 12/2019 |
| WO | WO 2019/239259 | 12/2019 |
| WO | WO 2019/241556 | 12/2019 |
| WO | WO 2019/243582 | 12/2019 |
| WO | WO 2019/243588 | 12/2019 |
| WO | WO 2020/003110 | 1/2020 |
| WO | WO 2020/011760 | 1/2020 |
| WO | WO 2020/011795 | 1/2020 |
| WO | WO 2020/011797 | 1/2020 |
| WO | WO 2020/016438 | 1/2020 |
| WO | WO 2020/028312 | 2/2020 |
| WO | WO 2020/028537 | 2/2020 |
| WO | WO 2020/030686 | 2/2020 |
| WO | WO 2020/030700 | 2/2020 |
| WO | WO 2020/030706 | 2/2020 |
| WO | WO 2020/064707 | 4/2020 |
| WO | WO 2020/064911 | 4/2020 |
| WO | WO 2020/073047 | 4/2020 |
| WO | WO 2020/089429 | 5/2020 |
| WO | WO 2020/132211 | 6/2020 |
| WO | WO 2020/187797 | 9/2020 |
| WO | WO 2020/198280 | 10/2020 |
| WO | WO 2020/219430 | 10/2020 |
| WO | WO 2020/234785 | 11/2020 |
| WO | WO 2020/242881 | 12/2020 |
| WO | WO 2020/243756 | 12/2020 |
| WO | WO 2021/046275 | 3/2021 |
| WO | WO 2021/062265 | 4/2021 |
| WO | WO 2021/067691 | 4/2021 |
| WO | WO 2021/119478 | 6/2021 |
| WO | WO 2021/150777 | 7/2021 |
| WO | WO 2021/152013 | 8/2021 |
| WO | WO 2022/056542 | 3/2022 |
| WO | WO 2022/063650 | 3/2022 |
| WO | WO 2022/072944 | 4/2022 |
| WO | WO 2022/074136 | 4/2022 |
| WO | WO 2022/076862 | 4/2022 |
| WO | WO 2022/076948 | 4/2022 |
| WO | WO 2022/109589 | 5/2022 |
| WO | WO 2022/109590 | 5/2022 |
| WO | WO 2022/109591 | 5/2022 |
| WO | WO 2022/173970 | 8/2022 |
| WO | WO 2022/174249 | 8/2022 |
| WO | WO 2023/278599 | 1/2023 |
| WO | WO 2023/014742 | 2/2023 |
| WO | WO 2023/049813 | 3/2023 |
| WO | WO 2023/076869 | 5/2023 |

OTHER PUBLICATIONS

International Search Report and Written Opinion received in PCT Application No. PCT/EP2019/066486, dated Sep. 25, 2019 in 15 pages.
International Preliminary Report on Patentability and Written Opinion received in PCT Application No. PCT/EP2019/066486, dated Dec. 30, 2020 in 10 pages.
Kong et al., "A Stein Equation Approach for Solutions to the Diophantine Equations," 2010 Chinese Control and Decision Conference, Xuzhou, May 26, 2010, pp. 3024-3028.
Koseli et al., "Online Viscosity Measurement of Complex Solutions Using Ultrasound Doppler Velocimetry", Turk J Chem, Jan. 2006, vol. 30, pp. 297-305.
McCormick et al., "Resolution of a 2/spl pi/ Ambiguity Problem in Multiple Frequency Spectral Estimation," in IEEE Transactions on Aerospace and Electronic Systems, Jan. 1995, vol. 31, No. 1, pp. 2-8.
Syrmos et al., "A Generalized Bezout Equation in Output Feedback Design," Proceedings of the 31st IEEE Conference on Decision and Control, Tucson, AZ, USA, Dec. 1992, vol. 4, pp. 3590-3594.
Udesen et al., "A Simple Method to Reduce Aliasing Artifacts in Color Flow Mode Imaging", IEEE Ultrasonics Symposium, 2005, Rotterdam, The Netherlands, Sep. 18-21, 2005, pp. 1352-1355.
"ABMD—Taking a Closer Look at Impella ECP as the Pivotal Trial Gets Underway", Guggenheim, Press Release, Mar. 29, 2022, pp. 4.
Vollkron et al., "Advanced Suction Detection for an Axial Flow Pump", Artificial Organs, 2006, vol. 30, No. 9, pp. 665-670.
Vollkron et al., "Development of a Suction Detection System for Axial Blood Pumps", Artificial Organs, 2004, vol. 28, No. 8, pp. 709-716.
Atkinson et al., "Pulse-Doppler Ultrasound and Its Clinical Application", The Yale Journal of Biology and Medicine, 1977, vol. 50, pp. 367-373.
Escudeiro et al., "Tribological behavior of uncoated and DLC-coated CoCr and Ti-alloys in contact with UHMWPE and PEEK counterbodies;" Tribology International, vol. 89, 2015, pp. 97-104.
Hinkel et al., "Pump Reliability and Efficiency Increase Maintenance Program—Utilizing High Performance Thermoplastics;" Proceedings of the 16th International Pump Users Symposium, Texas A&M University. Turbomachinery Laboratories; 1999, pp. 115-120.
Leguy et al., "Assessment of Blood Volume Flow in Slightly Curved Arteries from a Single Velocity Profile", Journal of Biomechanics, 2009, pp. 1664-1672.
Lombardi et al., "Flow Rate Profiler: an instrument to measure blood velocity profiles", Ultrasonics, 2001, vol. 39, pp. 143-150.
Murali, Akila, "Design of Inductive Coils for Wireless Power Transfer to Pediatric Implants", A graduate project submitted in partial fulfillment of the requirements For the degree of Master of Science in Electrical Engineering, California State University, Northridge, May 2018, pp. 37.
Mushi et al., "Identification of Fluidic Element Models to Simulate the Short-Term Baroreflex", Proceedings of the 45th IEEE Conference on Decision & Control, San Diego, CA, Dec. 13-15, 2006, pp. 6.
Neale, Michael J., "The Tribology Handbook;" 1999, Butterworth-Heinemann, Second Edition, pp. 582.
Park et al., "A Novel Electrical Potential Sensing Method for in Vitro Stent Fracture Monitoring and Detection", Jan. 1, 2011, vol. 21, No. 4, pp. 213-222.
Sak et al., "Influence of polyetheretherketone coatings on the Ti-13Nb-13Zr titanium alloy's bio-tribological properties and corrosion resistance;" Materials Science and Engineering: C, vol. 63, 2016, pp. 52-61.
Sinha et al., "Effect of Mechanical Assistance of the Systemic Ventricle in Single Ventricle Circulation with Cavopulmonary Connection", The Journal of Thoracic and Cardiovascular Surgery, Apr. 2014, vol. 147, No. 4, pp. 1271-1275.
"Understanding Hot-Wire Anemometry", Advanced Thermal Solutions, Inc., 2007, pp. 13-17.
Vieli, A., "Doppler Flow Determination", BJA: British Journal of Anaesthesia, 1988, vol. 60, pp. 107S-112S.

(56) References Cited

OTHER PUBLICATIONS

Yuanyuan et al., "Characteristics Analysis for Doppler Ultrasound Blood Flow Signals", China Medical Device Information, 5(1), Feb. 28, 1999, pp. 36-42.

Zhang, Dabiao et al., "Design of Microwave Velocity and Distance Monitor System", Instrument Technique and Sensor, Hebei Normal University, Apr. 25, 2004, pp. 3.

METHOD AND DEVICE FOR DETECTING A WEAR CONDITION OF A VENTRICULAR ASSIST DEVICE AND FOR OPERATING SAME, AND VENTRICULAR ASSIST DEVICE

BACKGROUND

Field

The invention relates to a device or a method related to detecting a state of wear of a cardiac support system.

Description of the Related Art

U.S. Pat. No. 5,904,708A describes a system with an implanted barometric pressure sensor, an extracorporeal barometric pressure sensor and an implanted processing unit that receives extracorporeal pressure and processes it to detect blood pressure changes. This system makes it possible to set or control a function of an implantable medical device using data from the implanted pressure sensor and the extracorporeal pressure sensor.

SUMMARY

Based on this, the underlying object of the invention is to further improve the methods and devices known in the state of the art for operating and in particular for monitoring the condition of a cardiac support system as well as a cardiac support system as such and to ensure high functional reliability and ideally avoid critical system failures.

With this in mind, the approach presented here introduces a method for detecting a state of wear of a cardiac support system, a method for operating a cardiac support system as well as a device that uses and/or controls said method and a cardiac support system described herein. Advantageous further developments and improvements are described herein.

Using the approach presented here, a sensor signal representing an operating state of a cardiac support system can be read and processed. The operating state can be a physical state of the cardiac support system, for example, or a state of an environment in which the cardiac support system is being operated. Using the sensor signal and a processing specification, a wear signal representing a state of wear of the cardiac support system can be determined, for example by comparing the sensor signal with a specific operating state of the cardiac support system. This advantageously makes it possible to continuously monitor the condition of the cardiac support system, for example in order to detect damage or aging of the cardiac support system or a wear process of the cardiac support system. This is useful for being able to avoid a failure of the cardiac support system or being able to take action quickly in the event of such a state of wear. The safety and reliability of the cardiac support system can advantageously be increased by monitoring the condition and detecting the state of wear.

The invention presents a method for detecting a state of wear of a cardiac support system. The method comprises a read-in step and a determination step. In the read-in step, a sensor signal representing an operating state of the cardiac support system is read-in. In the determination step, a wear signal is determined using the sensor signal and a comparison rule. The wear signal represents the state of wear.

The state of wear can be understood to be a current condition of the cardiac support system or of components of the cardiac support system, such as a rotor, a sliding bearing, an impeller or a cable, which can affect a function of the cardiac support system. In the case of the impeller, for example, this could be an imbalance of said impeller. The state of wear can also be understood to be a property for example, such as a position or location of the cardiac support system or a component of the cardiac support system, such as a pump inlet, for example to be able to detect whether the pump inlet has suctioned itself to a blood vessel. The cardiac support system can, for example, be a right ventricular support system or a left ventricular support system which can, for example, be designed as an apical cardiac support system or as a cardiac support system for an aortic valve position. The sensor signal can be an electrical signal or a radio signal, which can be provided by a sensor device of the cardiac support system, for example. The sensor device can comprise a temperature sensor, a pressure sensor or a voltage sensor, for example, and the sensor signal can accordingly represent a temperature, a pressure or a pressure change, or a voltage as the operating state. It is also possible for the sensor signal to include data from a plurality of sensors, for example. In the determination step, a sensor parameter set, for example, can be extracted using the sensor signal. To evaluate the sensor parameter set, the wear signal can be determined using the sensor parameter set. The wear signal can be an electrical signal which, as the state of wear, for example comprises a deviation of the state of wear from a predefined initial state of the cardiac support system that is stored in the form of the processing specification.

According to one embodiment, at least one wear parameter can be determined in the determination step. The wear signal can include the wear parameter. The wear parameter can comprise technical data relating to a component of the cardiac support system, for example, from which the condition of the component can be inferred. The operating state reflected by means of the sensor signal can be evaluated in terms of a temporal progression, for example. The wear parameter can advantageously be used to analyze the state of wear, for example to be able to predict a time of failure for the cardiac support system or a component of the cardiac support system, which increases safety. It is also possible to ascertain the state of wear of a specific component, for example, so as to be able to replace the relevant component instead of replacing the entire cardiac support system, which is advantageously resource- and cost-saving.

Additionally or alternatively, according to one embodiment, at least one functional parameter representing a functionality of the cardiac support system can be determined in the determination step. In this case, the wear signal may include the functional parameter. The functional parameter can indicate whether further reliable operation of the cardiac support system is possible, for example, or whether replacement or maintenance is necessary. The functionality of the cardiac support system can thus advantageously be monitored particularly easily. An impairment of the functionality of the cardiac support system or a desired functionality of the cardiac support system can therefore be detected, for example to avoid maintenance of an implanted cardiac support system or to be able to plan said maintenance ahead of time, which advantageously increases the safety and reliability of the cardiac support system.

According to one embodiment, the method can furthermore comprise a step of providing the sensor signal, and additionally or alternatively the wear signal, to an interface with an external processing device. The external processing device can be an extracorporeal control device, for example, or a portable device such as a smartphone, or a server or a warning device for the cardiac support system. The operating state and additionally or alternatively the state of wear can thus advantageously be stored externally, for example for further evaluation. For provision to an interface with the warning device or to the smartphone, the wear signal can include the functional parameter, for example, and for provision to an interface with the extracorporeal control device or the server, the wear signal can include the wear parameter, for example. The wear signal can additionally also include the functional parameter and the wear parameter, for example for provision to an interface with a smartphone, for example to visually or audibly display the wear signal. The wear signal can additionally or alternatively be determined for provision as a warning signal using a predefined limit value as a processing specification and as a function of a comparison result with said limit value, for example.

According to one embodiment, the method can also comprise a sensing step. In the sensing step, the operating state is sensed and the sensor signal representing the operating state is provided. For this purpose, a specific component or a specific region of the cardiac support system can be sensed, for example by means of a defined sensor region, in order to ascertain the operating state. A sensor device for acquiring the sensor signal can thus advantageously be set, for example to determine the state of wear of a component of the cardiac support system, or to determine the state of wear particularly accurately.

According to one embodiment, the sensor signal can also be sensed using a sensor device. The sensor device can be configured to sense an electrical quantity, a temperature, a pressure, a volume flow, a movement, an optical or acoustic signal, a force, or a change in position of the cardiac support system. A voltage can be sensed as the electrical quantity, for example. A pressure build-up or a pressure difference can be sensed as the pressure, for example. A vibration of a component of the cardiac support system can be sensed as a movement, for example, or a sudden movement in the form of a fall or a physical impact on a wearer of an implanted cardiac support system. Sensing the pressure and the volume flow is advantageous, for example, to ascertain whether the pump inlet of the cardiac support system has suctioned itself to a blood vessel. A displacement or malfunction of the cardiac support system, such as an imbalance of the impeller, can be identified with the aid of an optical or acoustic signal that can be acquired by a laser interferometer, a microphone or a structure-borne sound sensor, for example. To sense the mentioned quantities, the sensor device can, for example, comprise a voltage sensor, an electrical resistance sensor, a temperature sensor, a pressure sensor, an ultrasonic flow sensor, an optical reflection coefficient sensor, a movement sensor, an acceleration sensor, a magnetic sensor, a microphone, a force sensor, a distance sensor or an inductive and/or capacitive rotor bearing sensor or a combination of said sensors. At least one of said sensors can additionally also be configured to be redundant, for example for self-diagnosis of the sensors. Sensors integrated into the cardiac support system can advantageously be used to provide the sensor signal. This is cost-saving and makes a compact design of a device for carrying out this embodiment of the method possible.

According to one embodiment, the sensor signal can also represent the operating state in the time domain and additionally or alternatively in the frequency domain. For this purpose, the sensor signal can represent the operating state within a specific period of time, for example in order to ascertain an average value or a standard deviation of the operating state. If the sensor signal represents the operating state in the frequency domain, characteristic frequencies of a median frequency of the spectrum, the integrated band energy in defined frequency bands or also the absolute amplitude at the location of known damage frequencies can be determined, for example. A further analysis of the sensor signal is thus advantageously made possible, which is advantageous for an exact determination of the state of wear.

Furthermore, according to one embodiment, a further sensor signal representing a further operating state of the cardiac support system can be read-in in the read-in step. In the determination step, the wear signal can be determined using the sensor signal, the further sensor signal and the comparison rule. This is advantageous in order to be able to use a plurality of sensor signals to determine the state of wear.

In this case, according to one embodiment, a sensor parameter set can be extracted in the determination step using the sensor signal and the further sensor signal. The wear signal can be determined using the sensor parameter set and the comparison rule. Determining the sensor parameter set is advantageous for transforming the sensor data in the time or frequency domain.

According to one embodiment, the method can comprise a step of defining the comparison rule using the sensor signal. The sensor parameter set can be used to do this, for example. The sensor signal can be used to create a profile of the operating state, for example, or a so-called fingerprint of the system can be generated. This embodiment advantageously makes it possible to use a sensor signal that has already been read in to define the comparison rule; for example to set the comparison rule to a specific operating state, for example to an implanted state of the cardiac support system.

This approach further introduces a method for operating a cardiac support system. The method comprises the steps of one embodiment of the aforementioned method for detecting a state of wear of a cardiac support system and a step of providing a control signal for controlling a component of the cardiac support system. The control signal is output using the sensor signal or the wear signal. A sensor signal that is already required for the normal operation of the cardiac support system, i.e. a sensor signal that is required to perform a cardiac support function of the cardiac support system, can thus also be used to detect and optionally evaluate wear of the cardiac support system. According to this design example, a component and consequently a function of the cardiac support system can advantageously be adapted using the sensor signal and additionally or alternatively the wear signal, for example to reduce or prevent damage to a mechanical element of the cardiac support system, depending on the operating state or the state of wear. For example, the pump of the cardiac support system can be slowed using the sensor signal to prevent damage in the event of a detected impact, such as a fall, detected by an acceleration sensor or a movement sensor, for example.

The approach presented here further creates a device configured to carry out, control or implement the steps of a variant of a method for detecting a state of wear of a cardiac support system presented here or for operating a cardiac support system in corresponding devices. This design variant of the invention in the form of a device also makes it possible to achieve the underlying object of the invention quickly and efficiently.

For this purpose, the device can comprise at least one computing unit for processing signals or data, at least one memory unit for storing signals or data, at least one interface to a sensor or an actuator for inputting sensor signals from the sensor or for outputting data or control signals to the actuator, and/or at least one communication interface for inputting or outputting data embedded in a communication protocol. The computing unit can be a signal processor, a microcontroller or the like, for example, whereas the memory unit can be a flash memory, an EEPROM or a magnetic memory unit. The communication interface can be configured to input or output data in a wireless and/or wired manner, whereby a communication interface that can input or output wired data can, for example, input or output said data electrically or optically from or to a corresponding data transmission line.

In the present case, a device can be understood to be an electrical device that processes sensor signals and outputs control and/or data signals as a function of said sensor signals. The device can comprise an interface that can be hardware and/or software-based. In the case of a hardware-based configuration, the interfaces can be part of a so-called system ASIC, for example, which contains the various functions of the device. However, it is also possible for the interfaces to be separate, integrated circuits or consist at least in part of discrete components. In the case of a software-based configuration, the interfaces can be software modules that are, for example, provided on a microcontroller alongside other software modules.

Such a device can advantageously be part of a cardiac support system or integrated into a cardiac support system. For example, one embodiment of the device can be integrated into an already functional cardiac support system in order to be able to monitor the state of wear of the cardiac support system using sensor signals that are to be acquired anyway during the operation of the cardiac support system.

BRIEF DESCRIPTION OF THE DRAWINGS

Design examples of the approach presented here are shown schematically in the drawings and explained in more detail in the following description. The figures show.

DETAILED DESCRIPTION

In the following description of favorable design examples of the present invention, the same or similar reference signs are used for the elements shown in the various figures, which have a similar effect, whereby a repeated description of these elements is omitted.

Figure 1:
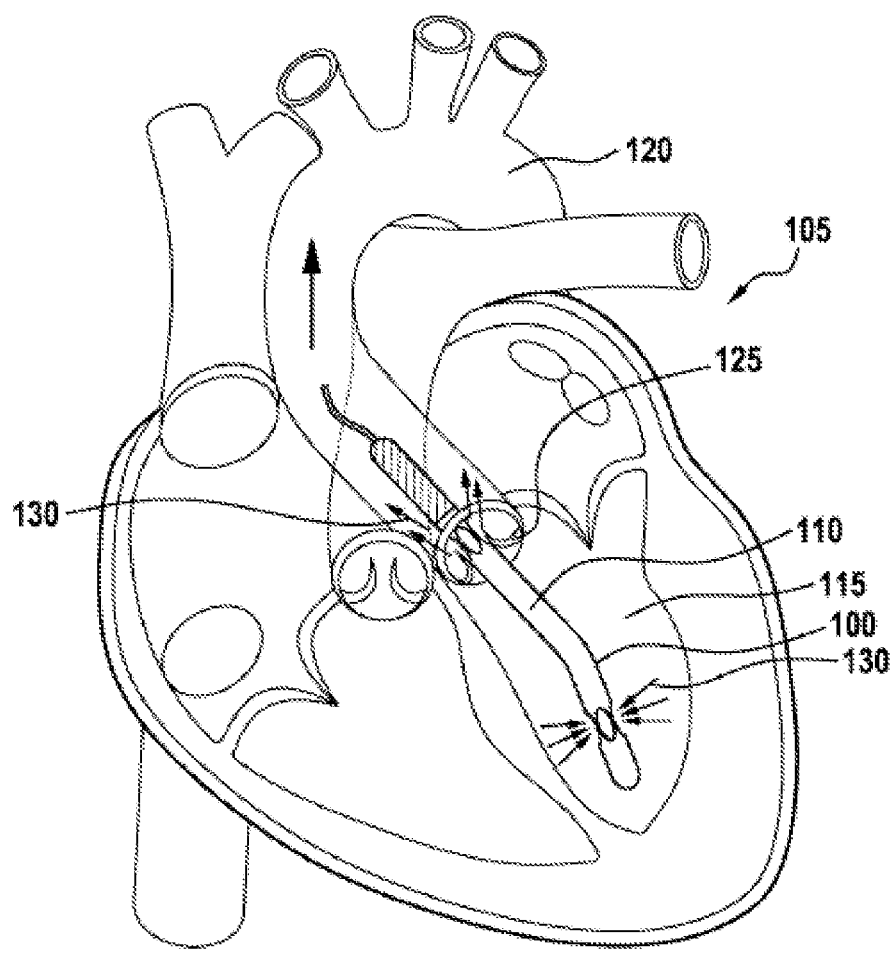
FIG. 1 a schematic illustration of a cardiac support system in aortic valve position according to one design example.

FIG. 1 shows a schematic illustration of a cardiac support system 100 in aortic valve position according to one design example. The figure shows a simple illustration of the cardiac support system 100 in the implanted state in a heart 105. In the aortic valve position of the cardiac support system 100 shown here, a section of the cardiac support system 100 with an inlet cannula 110 is disposed in the left ventricle 115 of the heart 105, and another section of the cardiac support system 100 is disposed in the aorta 120 in the region of the aortic valves 125. A pump volume flow 130 is received at the tip of the inlet cannula 110 in the ventricle 115 and discharged in the region of the aorta 120. One design example of the cardiac support system 100 shown here comprises a device for detecting a state of wear or for operating the cardiac support system 100, as shown with reference to FIGS. 3 and 4 described in the following.

Figure 2:
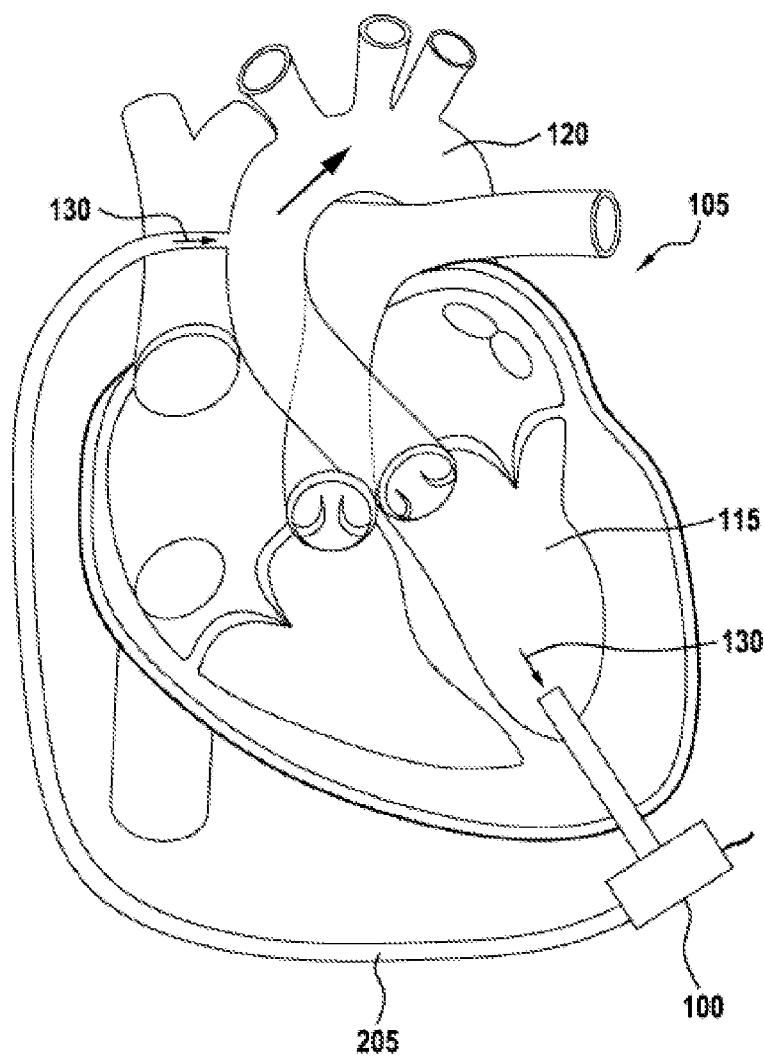
FIG. 2 a schematic illustration of an apical cardiac support system according to one design example.

FIG. 2 shows a schematic illustration of an apical cardiac support system 100 according to one design example. The figure shows a simple illustration of the cardiac support system 100 in the implanted state. The apical cardiac support system 100 comprises an input for introducing a blood flow, which pumps a blood flow from the left ventricle 115 of the heart into the aorta 120 via a drain cannula 205 which is led along the heart 105 outside the heart 105. For this purpose, the pump volume flow 130 is delivered to the drain cannula 205 by a pump of the cardiac support system 100, for example a rotary pump. The drain cannula 205 delivers the pump volume flow 130 to the aorta 120. One design example of the apical cardiac support system 100 shown here also comprises a device for detecting a state of wear or for operating the cardiac support system 100, as shown with reference to FIGS. 3 and 4 described in the following.

Figure 3:
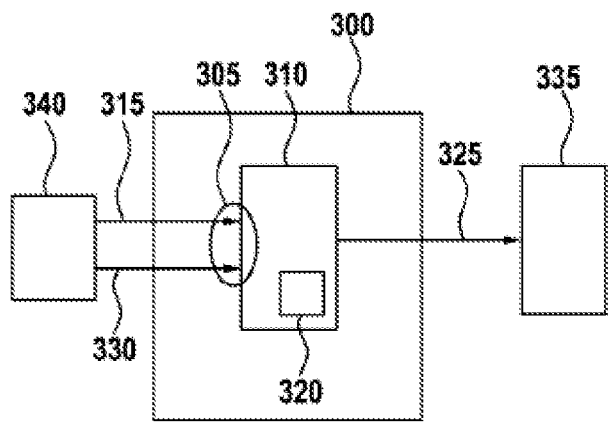
FIG. 3 a schematic illustration of a device for detecting a state of wear of a cardiac support system according to one design example.

FIG. 3 shows a schematic illustration of a device 300 for detecting a state of wear of a cardiac support system according to one design example. The device 300 comprises a reading device 305 and a determination device 310. The reading device 305 is configured to read in a sensor signal 315 that represents an operating state of the cardiac support system. The determination device 310 is configured to determine a wear signal 325 using the sensor signal 315 and a comparison rule 320. The wear signal 325 represents the state of wear.

The device 300 shown here can be used in conjunction with a cardiac support system such as one of the two cardiac support systems shown as an example in the preceding FIGS. 1 and 2.

According to one design example, the determination device 310 is configured to determine at least one wear parameter and to provide the wear signal 325 comprising the wear parameter. Additionally or alternatively, the determination device 310 is configured to determine at least one functional parameter representing a functionality of the cardiac support system and to provide the wear signal 325 comprising the functional parameter.

According to the design example shown here, the determination device 310 is also configured to provide the wear signal 325 to an interface with an external processing device 335. The sensor signal 315 is optionally also provided to the interface with the external processing device 335. The interface can be wireless or wired.

According to the design example shown here, the reading device 305 is also configured to read in at least one further sensor signal 330, which represents a further operating state of the cardiac support system. The determination device 310 is configured to determine the wear signal 325 using the sensor signal 315, the at least one further sensor signal 330 and the comparison rule 320. The determination device 310 is also optionally configured to extract a sensor parameter set using the sensor signal 315 and the at least one further sensor signal 330, and to determine the wear signal 325 using the sensor parameter set and the comparison rule 320. According to the design example shown here, the comparison rule is prestored in the determination device. The comparison rule 320 is optionally defined using the sensor signal 315.

According to the design example shown here, the sensor signal 315 and the further sensor signal 330 are provided by a sensor device 340. The sensor device 340 is optionally configured to sense the operating state and to provide the sensor signal 315 representing the operating state. According to one design example, the sensor device 340 is also configured to sense an electrical quantity, a temperature, a pressure, a volume flow, a movement, an optical or acoustic signal, a force, or a change in position of the cardiac support system in order to provide the sensor signal 315. According to one design example, the sensor signal 315 is configured to represent the operating state in the time domain and additionally or alternatively in the frequency domain.

In combination with a cardiac support system, the device 300 shown here can be used for monitoring at least one functional group of a cardiac support system so that a maintenance intervention can be carried out before the first symptoms or acute emergencies occur. The sensor device 340 can be a sensor device integrated into the cardiac support system, for example, and configured to determine operating parameters such as currents, voltages, temperatures, vibrations, pressures and pressure changes, sound, optical reflection coefficients, forces and changes in position. According to one design example, sensor parameters are extracted from the sensor data using the determination device 310, for example in the time domain and additionally or alternatively in the frequency domain.

A fingerprint of the system can, as it were, be generated from the determined sensor parameter set or the sensor parameter set can be regarded as such a fingerprint. Using the determination device 310, the fingerprint can continuously be compared to the definition of a healthy fingerprint in the form of the comparison rule 320. Deviations of the fingerprint from the healthy fingerprint of the comparison rule 320 are an indication of ongoing aging or damage processes of the cardiac support system. The temporal progression of the sensor parameter set is optionally employed using the determination device 310 to assess wear processes of the cardiac support system and possibly predict a time of failure. According to the design example shown here, the determination device 310 is configured to provide the wear signal 325 to the interface with the external processing device 335 to, in the event of a deviation from the normal fingerprint identified by means of the wear signal 325, for example in the form of the wear signal 325 comprising the wear parameter, inform the wearer of the implanted cardiac support system with the device 300, for example, the patient or a physician via the wear signal 325 representing the state of wear.

Such a monitoring of the condition of the cardiac support system using a variant of the device 300 shown here advantageously makes it possible to achieve a reduction or even a prevention of critical system failures. The early detection of a system degradation provides a time advantage, so that surgery appointments for component replacement, for example, can be planned early. Predictive maintenance interventions increases the patient's quality of life by not exposing the patient to a medical emergency scenario. The device 300 shown here can also be referred to as a condition monitoring system and provides an additional safeguard particularly for subsystems that cannot be configured to be redundant, such as the pump motor. By integrating the device 300 as a condition monitoring system, the patient's confidence in his support system can be increased, which results in a sense of security.

Using the wear signal 325, the determined state of wear can be transmitted via the interface with the external processing device 335 in the form of a communication interface, such as a radio modem or a wired interface. If the external processing device 335 comprises a display device, for example in the form of a screen of the extracorporeal control device or the portable device, a so-called "wearable", such as a smartphone coupled via Bluetooth Low Energy as an external processing device 335, the state of wear provided by means of the wear signal 325 can be displayed on the display device, for example in the form of a condition measure of the state of wear.

By providing the wear signal 325 to the interface with the external processing device 335, the state of wear and/or the underlying sensor values or sensor parameters can additionally or alternatively also be stored for later retrieval (via cable, radio, or an inductively coupled communication interface) in the extracorporeal control device or a control device implanted with the cardiac support system and/or can be transmitted via a wide area communication network (for example, WLAN, LTE, or GPRS) to a central server. The use of a central server has the advantage that the system fingerprint and the parameter trend progression of the sensor data and the state of wear transmitted by means of the wear signal 325 can be compared to a large population of systems, so that it is possible to make robust statements about the system state of the cardiac support system.

Figure 4:
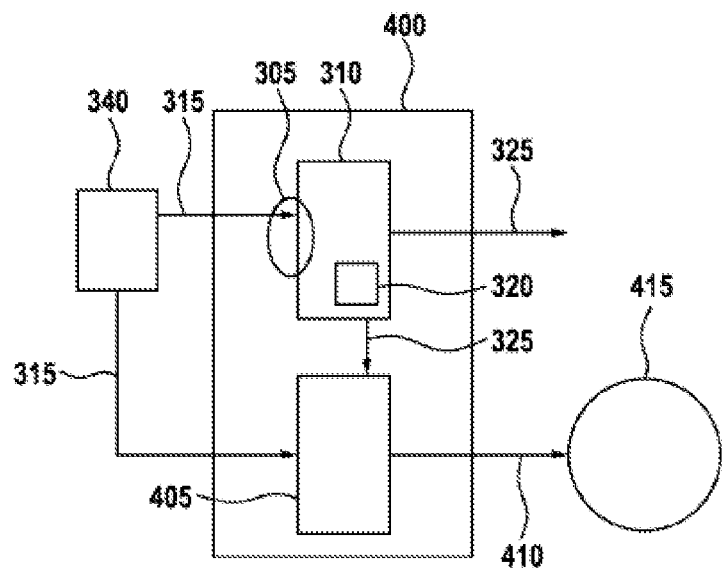
FIG. 4 a schematic illustration of a device for operating a cardiac support system according to one design example.

FIG. 4 shows a schematic illustration of a device 400 for operating a cardiac support system according to one design example. The device 400 shown here is configured to operate and additionally or alternatively control the cardiac support system, such as the cardiac support system shown as an example with reference to FIG. 1 or FIG. 2. For this purpose, the device 400 comprises the reading device 305 and the determination device 310, which correspond substantially to the reading device and the determination device shown in FIG. 3. The reading device 305 is correspondingly configured to read in the sensor signal 315 provided by the sensor device 340, and the determination device 310 is configured to determine and provide the wear signal 325 using the sensor signal 315 and the comparison rule 320.

According to the design example shown here, the device 400 also comprises a control device 405. The control device 405 is configured to provide a control signal 410 for controlling a component 415 of the cardiac support system using the sensor signal 315 or the wear signal 325.

The component 415 of the cardiac support system is a control unit, for example, or a structural element such as a pump or an impeller or a drive device as shown in the following FIG. 5. If, by means of the sensor signal 315 and additionally or alternatively by the determination of the wear signal 325 using the determination device 310, the device 400 detects a fall or other physical impact on the patient, the device 400 is configured to, using the control device 405, control one of the components 415 of the cardiac support system, such as the pump, by means of the control signal 410 to temporarily slow or stop the pump in order to prevent or reduce damage to the mechanical elements.

Figure 5:
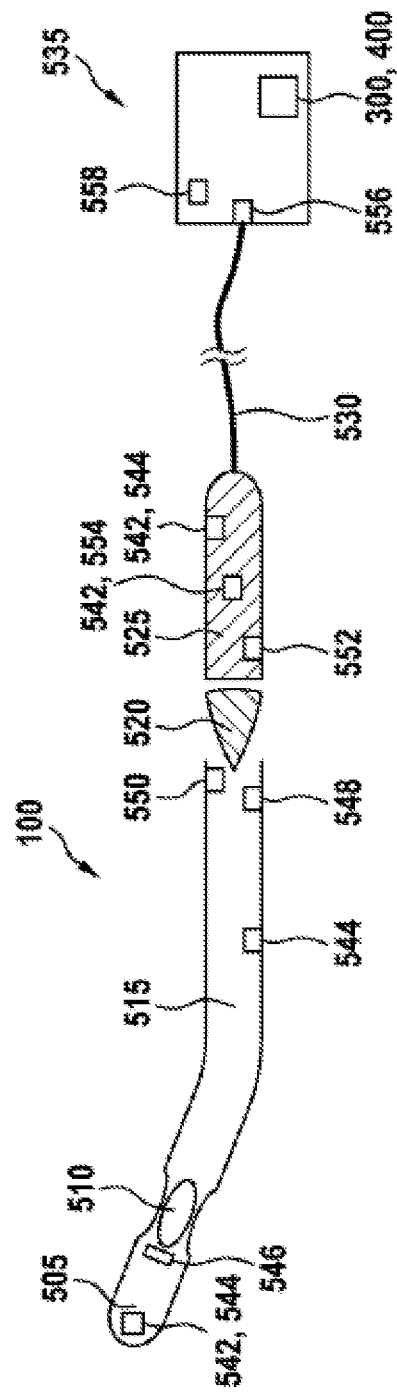
FIG. 5 a schematic illustration of an arrangement of sensors of a cardiac support system with a device for detecting a state of wear of a cardiac support system according to one design example.

FIG. 5 shows a schematic illustration of an arrangement of sensors of a cardiac support system 100 for a device 300 for detecting a state of wear of a cardiac support system 100 according to one design example. The example sensor integration into the cardiac support system 100 shown here can also be carried out in conjunction with the device 400 for operating the cardiac support system 100. The cardiac support system correspondingly comprises the device 300; 400, for example, which is similar to or the same as a variant of the device as described with reference to the preceding FIGS. 3 and 4. As an example, the cardiac support system 100 shown here is shown as a cardiac support system for the aortic valve position, like the cardiac support system described with reference to FIG. 1.

The cardiac support system 100 comprises a tip 505, an inlet cage 510 for receiving a blood volume flow, an inlet cannula 515 for delivering the blood volume flow to a micro-axial flow pump, an impeller 520 of the micro-axial flow pump, a magnetically or mechanically coupled electric drive 525, a supply cable 530 and a control unit 535. The control unit 535 comprises the device 300; 400, for example. As an example, the cardiac support system 100 comprises a variety of sensors as a sensor device in an example of a mounting position. According to the design example shown here, the cardiac support system 100 comprises three temperature sensors 542, two of which are disposed in the region of the electric drive 525 and one of which is disposed in the region of the tip 505. As an example, the cardiac support system 100 also comprises three pressure sensors 544, of which one is disposed in the region of the tip 505, one is disposed in the region of the inlet cannula 515 and one is disposed in the region of the electric drive 525. In the region between the tip 505 and the inlet cage 510, the cardiac support system also comprises an ultrasonic flow sensor 546. At an end facing away from the tip 505, the inlet cannula 515 additionally comprises a force, bending or distance sensor 548 and an optical reflection coefficient sensor 550. Adjacent to the impeller 520, the electric drive 525 comprises an impeller position sensor 552 in the form of a magnetic sensor or a Hall sensor, an optical distance sensor such as a laser interferometer, or an inductive and additionally or alternatively capacitive rotor position sensor. In the center of the electric drive 525, the cardiac support system 100 comprises a vibration sensor, a structure-borne sound sensor, a microphone and additionally or alternatively a microcontroller, for example in the form of a sensor hub, as a further impeller position sensor 554. In the region of the point of contact of the control unit 535 with the supply cable 530, the cardiac support system comprises a voltage sensor 556 in the form of a voltage, current, power, electrical resistance and/or back EMF sensor. The control unit 535 further comprises a control device sensor 558 in the form of a microphone, pressure, acceleration and/or rotation rate sensor, or temperature sensor.

A redundant design of the sensors 542, 544, 546, 548, 550, 552, 554, 556 and 558 shown here is advantageous for self-diagnosis of the sensors 542, 544, 546, 548, 550, 552, 554, 556 and 558 using deviations between the individual sensor values. An integration of all of the sensors 542, 544, 546, 548, 550, 552, 554, 556 and 558 shown here does not make sense in every application or, for reasons of installation space or cost, cannot be implemented in every application. The most relevant sensors can be selected in a targeted manner depending on the specific application, for example on the basis of a failure mode and effects analysis (FMEA analysis) or observed failures in long-term tests or stress tests.

The following is a list of application examples for the device 300, 400 in conjunction with the cardiac support system 100 and a sensor device such as one or more of the sensors 542, 544, 546, 548, 550, 552, 554, 556 and 558 shown here for detecting the state of wear of the cardiac support system 100 and/or for operating the cardiac support system 100:

The impeller sensor 554 in the form of the microphone or the structure-borne sound sensor and additionally or alternatively the control device sensor 558 in the form of the microphone and/or an acceleration sensor enables an analysis of the bearing wear by determining the state of wear.

In the case of magnetically coupled and magnetically mounted impellers 520, aging and deposits and the onset of pump thromboses can result in an imbalance of the impeller 520, which can be detected via the microphone, the acceleration sensor, the rotation rate sensor and the structure-borne sound sensor of the impeller sensor 554 and/or the control device sensor 558.

A change in friction in the sliding bearings of the cardiac support system 100, for example as a result of wear or the build-up of deposits, can be detected via a change in the power consumption, which can be sensed by a voltage sensor 556 in the form of a current, voltage, or power sensor, in combination with the actual pressure build-up or volume flow build-up, which can be sensed by one of the pressure sensors 544 in the region of the inlet cannula 515 or the electric drive 525 or the ultrasonic flow sensor 546. This error pattern furthermore also leads to a characteristic oscillation, which can be detected by the microphone, the acceleration sensor, the rotation rate sensor and the structure-borne sound sensor of the impeller sensor 554 and/or the control device sensor 558.

A measurement of the slippage between the magnetically coupled drive 525 and the impeller 520 provides information about the condition of the coupling and the sliding bearings of the impeller 520. The slippage can be sensed via an optical, magnetic or capacitive impeller position sensor 552, for example, or the phase relationship of the electric drive current and the back-induced field energy (back EMF) in currentless turns of the multiphase electric motor 525 can be sensed by means of the voltage sensor 556, for example in the control device 535 or in the electric drive 525. For this purpose, the voltage sensor 556 can be placed in the position shown here or in the region of the electric drive 525 in the position of the temperature sensor 542 or pressure sensor 554 disposed there.

A load on the bearings and a resulting pressure build-up of the impeller 520 can also be sensed at the bearing of the impeller by means of the force, strain or distance sensors 548.

Deposits and the onset of pump thromboses can be detected via a pressure drop in the inlet hose in the form of the inlet cannula 515, for example via pressure gradients between the aorta and the inlet cannula 515 or the ventricle, but also via a comparison of the electrical power consumption detectable by means of the voltage sensor 556 with the actual flow detectable by means of the ultrasonic flow sensor 546 and the pressure build-up of the pump detectable by means of the pressure sensors 544.

Indications of aging processes in the stator of the electric drive 525 are provided by the winding temperature that can be detected by means of the temperature sensor 542 positioned in the region of the electric drive 525, for example, or the winding impedance that can be detected by means of the voltage sensor 556, but also by optically, inductively or capacitively measured dimensions of the motor air gap measured by means of an impeller position sensor 552 in the position of the temperature sensor 542 or pressure sensor 544 disposed in the region of the electric drive 525.

Deposits on the rotor, as well as an imbalance, can also be determined via optical measurement of the reflection coefficient using the reflection coefficient sensor 550.

The quality of the supply cable 530 can be monitored via an electrical resistance measurement by means of the voltage sensor 556. In addition to detecting cable breaks (series measurement), the resistance measurement can also be carried out as a complex-valued impedance measurement between adjacent line strands to assess the condition of the insulation jacket and/or dielectric.

Faults in the power and signal electronics of the control device 535 can be detected by measuring the temperature of individual assemblies and monitoring selected voltage levels.

Suctioning of a pump inlet to the ventricular wall of the aorta in a cardiac support system 100 in aortic valve position, a so-called "suction", can also be detected by means of the device 300, 400 shown here. A supporting blood volume flow is no longer possible if the cardiac support system 100 suctions on; the cardiac support system 100 should (automatically) reduce the pump power until said system releases from the aortic wall. Suctioning on can be detected via the pressure gradient of the pressure sensors in the region of the tip 505 and in the region of the inlet cannula 515 and by means of the ultrasonic flow sensor 546. Partial closure of the inlet cage 510 also changes the flow conditions in the inlet cage 510, which can be detected via the Doppler spectrum of the ultrasonic flow sensor 546.

The sensor data processing by means of the determination device of the device 300, 400 is based on the analysis of the sensor signals in the time domain, for example via relative or absolute threshold values, mean values, standard deviations, minimum and maximum values in time windows or the overall observation period. Additionally or alternatively, the sensor data processing by means of the determination device of the device 300, 400 is based on the analysis of the sensor signals in the frequency domain, for example via a determination of characteristic frequencies, a median frequency of the spectrum, the integrated band energy in defined frequency bands or also the absolute amplitude at the location of known damage frequencies. The mentioned sensor parameters of the operating state can be determined on the basis of predefined threshold values of the comparison rule as condition parameters, i.e. as wear parameters, for example. Alternatively, a fingerprint of the system parameters can also be defined as a comparison rule and, for example, a threshold value can be defined on a mathematical distance measure on the fingerprint defined as healthy, for example as a threshold value hyperplane in the multidimensional parameter space.

The processing of the sensor values can be realized in a pump-integrated microcontroller such as a sensor hub or in the control device 535. The sensor hub can also be used only for preprocessing the sensor data and forwarding extracted sensor parameters, which reduces the required communication bandwidth along the supply cable 530.

Figure 6:
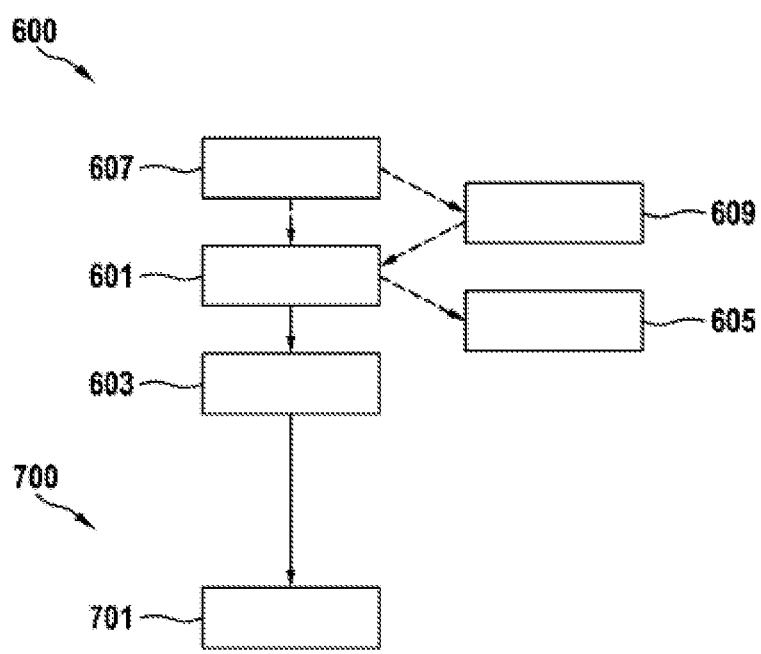
FIG. 6 a flow diagram of a method for detecting a state of wear of a cardiac support system and a method for operating a cardiac support system according to one design example.

FIG. 6 shows a flow diagram of a method 600 for detecting a state of wear of a cardiac support system and a method 700 for operating a cardiac support system according to one design example.

The method 600 comprises a read-in step 601 and a determination step 603. In the read-in step 601, a sensor signal representing an operating state of the cardiac support system is read-in. In the determination step 603, a wear signal is determined using the sensor signal and a comparison rule. The wear signal represents the state of wear.

According to one design example, at least one wear parameter is determined in the determination step 603. In this case, the wear signal includes the at least one wear parameter. In the determination step 603, at least one functional parameter representing a functionality of the cardiac support system is optionally determined as well. The wear signal then comprises the at least one functional parameter.

The method 600 also optionally comprises a step 605 of providing the sensor signal and/or the wear signal to an interface with an external processing device. The provision step 605 optionally takes place after the determination step 603. If only the sensor signal is provided in the provision step 605, the provision step 605 can also take place subsequent to the read-in step 601.

According to one design example, the method 600 further comprises a sensing step 607, in which the operating state is sensed and the sensor signal representing the operating state is provided. The sensing step 607 optionally takes place before the read-in step 601. The sensing step 607 is additionally or alternatively carried out before the provision step 605.

In the read-in step 601, a further sensor signal representing a further operating state of the cardiac support system is optionally read-in. In this case, the wear signal is determined in the determination step 603 using the sensor signal, the further sensor signal and the comparison rule. A sensor parameter set is optionally also extracted in the determination step 603 using the sensor signal and the further sensor signal. The wear signal is then determined using the sensor parameter set and the comparison rule.

According to one design example, the method 600 further comprises a step 609 of defining the comparison rule using the sensor signal. The defining step 609 is optionally carried out after the read-in step 601 before the determination step 603.

The method 700 for operating a cardiac support system comprises at least step 601 and step 603 of the method 600 and optionally one or more of steps 605, 607 and 609 as described above. The method 700 further comprises a step 701 of providing a control signal for controlling a component of the cardiac support system. The control signal is provided using the sensor signal or the wear signal.

If a design example includes an "and/or" conjunction between a first feature and a second feature, this should be read to mean that the design example according to one embodiment comprises both the first feature and the second feature and, according to another embodiment, comprises either only the first feature or only the second feature.

The invention claimed is:

1. A method for controlling a cardiac support system, the method comprising:
   determining, using a first sensor signal at a first time from a first sensor of the cardiac support system, a first operating state, wherein the first operating state is associated with an impeller of the cardiac support system implanted into a heart;
   receiving a second sensor signal at a second time from a second sensor of the cardiac support system, the second sensor signal associated with a second operating state of a component of the cardiac support system;
   determining a wear signal based at least in part on the first sensor signal, the second sensor signal, and a comparison rule, wherein the wear signal is associated with the state of wear of the component of the cardiac support system; and
   controlling the component of the cardiac support system associated with the second sensor signal with a control signal based on the wear signal.

2. The method of claim 1, wherein the first sensor signal is associated with deposits on the impeller or an imbalance of the impeller.

3. The method of claim 1, wherein the first sensor signal is associated with at least one of: position, vibration, acceleration, pressure, rotation rate, temperature, voltage, current, power, optical reflection, or electrical resistance associated with the impeller.

4. The method of claim 1, wherein the second sensor signal is further associated with an inlet cannula of the cardiac support system.

5. The method of claim 4, wherein the second sensor signal is associated with a change in flow or pressure in the inlet cannula.

6. The method of claim 1 further comprising:
providing the first sensor signal or the wear signal to an external processing device.

7. The method of claim 1, wherein the first sensor signal represents the operating state of the cardiac support system in the time domain or the frequency domain.

8. The method of claim 1 further comprising:
determining a characteristic oscillation in changes of the first operating state of the cardiac support system, and wherein the characteristic oscillation is associated with an error pattern of the first operating state.

9. The method of claim 1 further comprising:
generating a fingerprint based at least in part on the first sensor signal;
comparing the fingerprint with a healthy fingerprint based at least in part on the comparison rule; and
determining the wear signal based at least in part on the comparison between the fingerprint and the healthy fingerprint.

10. The method of claim 1 further comprising:
generating a control signal configured to control a component of the cardiac support system, the control signal generated based at least in part on the wear signal; and
transmitting the control signal for controlling a component of the cardiac support system.

11. A cardiac support system, the cardiac support system comprising:
an impeller;
a first sensor associated with the impeller;
a component;
a second sensor associated with the component; and
a control device configured to:
determine, using a first sensor signal at a first time from the first sensor, a first operating state of an impeller of the cardiac support system;
receive a second sensor signal at a second time from the second sensor of the cardiac support system, the second sensor signal associated with a second operating state of a component of the cardiac support system;
determine a wear signal based at least in part on the first sensor signal, the second sensor signal, and a comparison rule, wherein the wear signal is associated with the state of wear of the component of the cardiac support system; and
control the component of the cardiac support system associated with the second sensor signal with a control signal based on the wear signal.

12. The system of claim 11, the control device further configured to:
generate and transmit the control signal to the cardiac support system.

13. The system of claim 11, wherein the first sensor signal is associated with deposits on the impeller of the cardiac support system.

14. The system of claim 11, wherein the first sensor signal represents the operating state of the cardiac support system in the time domain or the frequency domain.

15. The system of claim 11, wherein the second sensor signal is further associated with an inlet cannula of the cardiac support system.

16. A cardiac support system comprising:
an inlet cannula for delivering blood volume flow to a flow pump;
an impeller of the flow pump; and
a device configured to determine a state of wear of a cardiac support system, the device comprising:
a reading device configured to receive a first sensor signal associated with a first operating state of the impeller of the cardiac support system and a second sensor signal associated with a second operating state of the cardiac support system; and
a determination device configured to determine a wear signal based at least in part on the first sensor signal, the second sensor signal, and a comparison rule; and
a control device configured to generate and transmit a control signal to the cardiac support system and control a component of the cardiac support system based on the control signal, wherein the control signal is generated based at least in part on the wear signal.

17. The system of claim 16, wherein the first sensor signal is associated with an operating state of the impeller of the cardiac support system.

18. The system of claim 16, wherein the first sensor signal represents the operating state of the cardiac support system in the time domain or the frequency domain.

19. The system of claim 16, wherein the second sensor signal is associated with an operating state of the inlet cannula of the cardiac support system.

* * * * *